(12) United States Patent
Gasser et al.

(10) Patent No.: US 6,204,373 B1
(45) Date of Patent: Mar. 20, 2001

(54) PLANT PROMOTERS

(76) Inventors: Charles Scott Gasser, 3301 Seabright Ave., Davis, CA (US) 95616; Kim Anne Budelier; Dorian A. Gunning, both of 4 Featherbed Ct., Lawrenceville, NJ (US) 08648

( * ) Notice: Subject to any disclaimer, the term of this patent is extended or adjusted under 35 U.S.C. 154(b) by 0 days.

(21) Appl. No.: 07/517,918

(22) Filed: May 2, 1990

(51) Int. Cl.$^7$ .............................. C12N 15/11; A01H 5/00
(52) U.S. Cl. ........................................... 536/24.1; 800/288
(58) Field of Search ................... 536/27, 24.1; 800/205, 800/278, 288, 320.1; 435/172.1, 172.3, 68, 91; 935/22, 35, 64, 67

(56) References Cited

FOREIGN PATENT DOCUMENTS

0193259 * 9/1986 (EP) .............................. C12N/15/00
0242062 * 10/1987 (EP) .
0242991 * 10/1987 (EP) .

OTHER PUBLICATIONS

Bird et al. (Bird), "The Tomato Polygalacturonase Gene and Ripening–Specific Expression in Transgenic Plants," *Plant Molecular Biology*, vol. 11, pp. 651–662 (1988).*

Reech et al. Cell vol. 50 pp. 667, (1987).*

Fishboff et al. (1987) Biotechnology vol. 5 pp. 807–813.*

Koletsky et al. (1986). The Journal of Immuniology vol. 137—p. 1054–1059 #3.*

Hoandler et al. (1987) The Embo Journal. vol. 6#4 pp. 947–950.*

Boswell et al. (1988) In. Computerized Molecular Biology Sources & Methods for Sequence Analysis. Edelto Arthur M. Lesk. pp. 170–171. Oxford University Press.*

* cited by examiner

Primary Examiner—Gary Benzion
(74) Attorney, Agent, or Firm—Lawrence M. Lavin; Howrey Simon Arnold & White, LLP

(57) ABSTRACT

The invention provides plant cyclophilin promoters that direct efficient expression of contiguous structural coding sequences in essentially all plant cells and plant organs of transgenic plants. In addition, chimeric genes containing the plant cyclophilin promoters of the invention and vectors comprising the plant cyclophilin promoters and chimeric genes of the invention are taught herein.

22 Claims, 4 Drawing Sheets

```
                 1                                                          50
Consensus        ATGGc.AAcC  Ctaa.GTtTt  cTTcGACaTg  ACCgTcGGcG  gcgcacC.GC
Maize            ATGGCGAACC  CTCGGCGTCTT CTTCGACATG  ACCGTCGGCG  GCGCCCCGGC
B. napus         ATGGTTAACC  CTAAAGTTTA  TTTCGACATG  ACCGTTGGCG  ACAAAGCCGC
Tomato           ATGGCAAATC  CAAAGGTTTT  CTTTGACCTT  ACCATCGGTG  GTGCACCAGC 51                                                        100
Consensus        .GGcCG.aTc  GTGATGGAGC  T.TaCGCCgA  cac.gt.CCC  aAgACcGC.G
Maize            GGGCCGGATC  GTGATGGAGC  TGTACGCCAA  CGAGGTGCCC  AAGACCGCGG
B. napus         CGGCCGCATC  GTGATGGAGC  TTTACGCCGA  CACAGTCCCC  GAGACGGCCG
Tomato           TGGTCGTGTG  GTGATGGAGC  TCTTCGCCGA  TACCACTCCC  AAAACCGCTG 101                                                       150
Consensus        AGAACTTCCG  .GCtCT.TGc  ACCGGcGAGA  aaGG.gT.GG  cAAgtccGGg
Maize            AGAACTTCCG  CGGCGCTGTGC ACGGGCGAGA  AGGGCGTGGG  CAAGTCCGGG
B. napus         AGAACTTCCG  TGCTCTCTGC  ACCGGCGAGA  GAGGAATCGG  CAAATCCGGA
Tomato           AGAACTTCCG  AGCTCTTTGT  ACCGGTGAGA  AAGGTGTTGG  AAAGATGGGG 151                                                       200
Consensus        AAGCC.cTcC  ACTACAAGGG  CTC.aCCTTC  CACCGcGTgA  TCCCCgaGTT
Maize            AAGCCGCTCC  ACTACAAGGG  CTCCACCTTC  CACCGCGTCA  TCCCCGAGTT
B. napus         AAGCCACTCC  ACTACAAGGG  CTCGGCTTTC  CACCGCGTGA  TCCCCAAGTT
Tomato           AAGCCTTTGC  ACTACAAGGG  CTCAACCTTC  CACCGTGTGA  TCCCAGGGTT
```

Figure 1

```
          201
Consensus  CATGTGcCAa  GGaGG.GAtT  TCACCgcCGG  .AACGGaaCg  GGaGGaGAGT  250
Maize      CATGTGCCAG  GGCGGGCGACT TCACCCCGGG  CAACGGCACC  GGCGGCGAGT
B. napus   CATGTGCCAA  GGAGGAGATT  TCACCGCCGG  GAACGGAACG  GGAGGAGAGT
Tomato     CATGTGTCAA  GGAGGTGATT  TCACCGCCGG  AAACGGACCG  GgAgGAGAGT 251
Consensus  CgATCTAcGG  cg.gAAgTTC  aacGAcGAGA  ACTTcGT.aa  gAAGCAcaCC  300
Maize      CCATCTACGG  CGAGAAGTTC  CCCGACGAGA  AGTTCGTGCG  CAAGCAACCC
B. napus   CGATCTACGG  CATGAAGTTC  AAAGACGAGA  ACTTTGTCAA  GAAGCACACC
Tomato     CGATCTATGG  AGCCAAATTC  AACGATGAGA  ACTTCGTTAA  GAAGCACACC 301
Consensus  GgcCC.GGta  T.CTCTCCAT  GgctAAcGct  GG.cC.aacA  CCAACGG.tc  350
Maize      GCCCCCGGTG  TGCTCTCTCCAT GGCCAACGCC  GGGCCCAACA  CCAACGGCTC
B. napus   GGTCCGGGTA  TTCTCTCTCCAT GCGTAACGCT  GGTTCGAACA  CGAACGGATC
Tomato     GGCCCTGGAA  TCCTCTCCAT  GGCTAATGCT  GGACCTGGAA  CCAACGGTCT 351
Consen     tCAGTTtTTC  ATcTGcACCG  ..aaGAC..c  gTggctcgac  gg.aagca.g  400
Maize      CCAGTTCTTC  ATCTGCACCG  TCGCGACCCC  TTGGCTCGAC  GGCAAGCACG
B. napus   TCAGTTTTTC  ATTTGCACTG  AGAAGACATC  GTGGCTCGAC  GGGAAGCATG
Tomato     TCAGTTTTTC  ATCTGTACCG  CTAAGACTGA  GT........  ..........

Figure 1 continued
```

```
           401                                                         450
Consensus  t.gt.ttcgg  .ca.gt.gtc  ga.gg.atgg  a.gtcgt.a.  .g.cat.gag
Maize      TCGTCTTCGG  CCAGGTCGTC  GAGGGCATGG  ACGTCGTCAA  GGCCATCGAG
B. napus   TTGTGTTCGG  TCAAGTTGTC  GAAGGGATGG  ATGTCGTTAG  AGACATTGAG
Tomato     ..........  ..........  ..........  ..........  ..........

451                                                         500
Consensus  aaggt.gg..  c...ca..gg  ...ac.tc.   aag..ggt..  .g..c..tga
Maize      AAGGTGGGCA  CCCGCAACGG  CTCCACCTCC  AAGGTGGTCA  AGGTCGCTGA
B. napus   AAGGTTGGAT  CTGACAGTGG  AAGGACTTCT  AAGAAGGTTG  TGACCTGTGA
Tomato     ..........  ..........  ..........  ..........  ..........

501          519
Consensus  ctg.gg.cag  ct....tag
Maize      CTGCGGACAG  CTCTCCTAG
B. napus   CTGTGGTCAG  CT...TTAG
Tomato     ..........  .........

Figure 1 continued
```

```
              1
Consensus     MaNPkVfFDm  TvGgapAGRi  VMELyAdtvP  kTAENFRALC  TGEkGvGKsG
Maize         MANPRVFFDM  TVGGAPAGRI  VMELYANEVP  KTAENFRALC  TGEKGVGKSG
B. napus      MVNPKVYFDM  TVGDKAAGRI  VMELYADTVP  ETAENFRALC  TGERGIGKSG
Tomato        MANPKVFFDL  TIGGAPAGRV  VMELFADTTP  KTAENFRALC  TGEKGVGKMG 51                                                    100
Consensus     KPLHYKGStF  HRVIP.FMCQ  GGDFTaGNGt  GGESIYG.KF  .DEnFVkKht
Maize         KPLHYKGSTF  HRVIPEFMCQ  GGDFTRGNGT  GGESIYGEKF  PDEKFVRKQP
B. napus      KPLHYKGSAF  HRVIPKFMCQ  GGDFTAGNGT  GGESIYGMKF  KDENFVKKHT
Tomato        KPLHYKGSTF  HRVIPGFMCQ  GGDFTAGNGP  GGESIYGAKF  NDENFVKKHT 101                                                   150
Consensus     gPGiLSMaNA  GpnTNGsQFF  ICT.kT.WLD  GKHVVFGQVV  EGMDVV..IE
Maize         APGVLSMANA  GPNTNGSQFF  ICTVATPWLD  GKHVVFGQVV  EGMDVVKAIE
B. napus      GPGILSMRNA  GSNTNGSQFF  ICTEKTSWLD  GKHVVFGQVV  EGMDVVKAIE
Tomato        GPGILSMANA  GPGTNGLQFF  ICTAKTE...  ........    ........

151           173
Consensus     KVG...G.TS   K.V...DCGQ  L.*
Maize         KVGTRNGSTS   KVVKVADCGQ  LS*
B. napus      KVGSDSGRTS   KKVVTCDCGQ  L*.
Tomato        ........     ........    .

Figure 2
```

PLANT PROMOTERS

BACKGROUND

The invention relates to plant promoters. Promoters are critical elements for constructing novel genetic constructs, such as chimeric genes, for introduction of useful traits into plants. A critical element for construction of an effective chimeric gene is an appropriate promoter element capable of directing transcription of a protein coding sequence at an appropriate level in target tissues. Constructs containing useful chimeric genes include those capable of conferring useful traits such as insect tolerance (D. A. Fischhoff et al., *Biotechnology* 5:807 (1987)), tolerance to viral infection (P. Powell-Abel et al., *Science* 232:738 (1986)), and tolerance to herbicides.

Those skilled in the art will recognize that promoters used in attempts to obtain high-level constitutive expression of chimeric genes in plants include the promoter of the 35S gene of cauliflower mosaic virus (35S) and the mannopine synthase promoter from *Agrobacterium tumefaciens* (MAS). Both of these promoters have been used to engineer expression of glyphosate tolerance (D. M. Shah et al., *Science* 233;478 (1986) and L. Comai et al., *Nature* 317:741 (1985)) and insect tolerance (D. A. Fischhoff et al., *Bio/Technology* 5:807 (1987) and M. Vaeck et al., *Nature* 238:33 (1987)). The promoters previously used, however, have not been successful in expressing in essentially all organs of a plant.

Promoter sequences able to direct chimeric gene expression in specific tissues have been described by Benfey and Chua, *Science* 244:174 (1989), by Verma and Goldberg, Eds., *Temporal and Spatial Regulations of Plant Genes* (Springer-Verlag, New York (1988) and by Goldberg, *Science* 240:1460 (1988). Other examples include the work on insect tolerance, described above, in which only toxicity of the leaves and fruits was demonstrated. Expression in specific tissues is not useful for applications requiring expression in virtually all organs of a plant.

A specific example of an application in which expression in all organs of a plant would be preferred is the engineering of insect tolerance utilizing the insect control protein of *Bacillus thuringiensis* (D. A. Fischhoff et al., (1987). In cases where insects feed on all parts of the plant, a chimeric gene which is expressed in all organs would be most effective in protecting the plant from damage. A second example is that of herbicide tolerance.

The promoters of this invention direct efficient expression of contiguous structural genes in transgenic plants and plant cells and also provide efficient expression in essentially all plant organs.

SUMMARY OF THE INVENTION

The invention provides plant cyclophilin promoters that direct efficient expression of contiguous structural coding sequences in essentially all plant cells and plant organs of transgenic plants. In addition, chimeric genes containing the plant cyclophilin promoters of the invention and vectors comprising the plant cyclophilin promoters and chimeric genes of the invention are taught herein.

BRIEF DESCRIPTION OF FIGURES

FIG. 1 Comparison of coding sequences of cDNA clones for cyclophilin genes from tomato, *Brassica napus* and maize. An upper case letter in the consensus sequence indicates complete identity, a lower case letter in the consensus sequence indicates two out of three sequences are the same, and a period (".") in the consensus sequence indicates no identity. A period (".") in the plant sequences indicates a gap and is inserted to provide maximum comparisons. The periods at the 3' end of the tomato sequence represent a region for which the sequence has not been determined.

FIG. 2 Comparison of amino acid sequences of deduced plant cyclophilin proteins from tomato, *Brassica napus* and maize. An upper case letter in the consensus sequence indicates complete identity, a lower case letter in the consensus sequence indicates two out of three sequences are the same, and a period (".") in the consensus sequence indicates no identity. A period (".") in the plant sequences indicates a gap, and an asterisk ("*") indicates a stop codon. The periods at the 3' end of the tomato sequence represent a region for which the sequence has not been determined.

DESCRIPTION OF THE INVENTION

This invention provides plant cyclophilin promoters. More particularly, the invention provides promoters of plant cyclophilin genes that direct efficient expression of attached heterologous coding sequences in essentially all plant cells in all plant organs of transgenic plants in essentially all stages of development.

The following terms are defined as used herein:

Promoter or promoter region refers to a DNA sequence capable of promoting transcription of a contiguous structural coding sequence to produce messenger RNA (mRNA). As contemplated herein, a promoter or promoter region includes variations of promoters derived by means of ligation to various operator regions, random or controlled mutagenesis and addition or duplication of enhancer sequences.

Plant cyclophilin promoter is defined by the ability of a cyclophilin probe, based on cyclophilin DNA or amino acid sequences, to hybridize to a homologous cyclophilin gene wherein the promoter is located upstream (5') of the cyclophilin coding sequence and is capable of driving transcription of coding sequences under its control when introduced into a host as part of a suitable recombinant vector, as demonstrated by its ability to produce mRNA. A Cyclophilin gene refers to a gene encoding a protein with greater than about 65% amino acid sequence identity to mammalian cyclophilin (B. Haendler et al., *EMBO J* 6:947 (1987)).

Recombinant vector refers to any agent capable of genomic integration or autonomous replication, including but not limited to plasmids, comprising a DNA molecule to which one or more DNA segments can be added (operatively linked). Transformation refers to the introduction of DNA into a recipient host or hosts. Host or hosts refers to entire plants, plantlets or plant parts such as callus, roots, tubers, propagules, seed, seedlings, pollen, plant tissues or plant cells.

Hybridization refers to the ability of a nucleic acid strand to join with a complementary strand through base pairing. Hybridization takes place when complementary sequences between the hybridizing agent (probe) and the target nucleotide sequence bind to one another.

For purposes of the description and claims, the nomenclature referenced in *The Journal of Biological Chemistry* 260:14 (1983) as set forth herein will be used to identify the naturally occurring amino acids: alanine (Ala;A), asparagine (Asn:N), aspartic acid (Asp;D), arginine (Arg;R), cysteine (Cys;C), glutamic acid (glu;E), glutamine (Gln:Q), glycine (Gly;G), histidine (His,H), isoleucine (Ile;I), leucine (Leu;L), lysine (Lys;K), methionine (Met;M), phenylalanine (Phe;F), proline (Pro;P), serine (Ser;S), threonine (Thr;T), tryptophan (Trp;W), tyrosine (Tyr;Y), and valine (Val;V).

All peptide structures represented herein are shown in conventional format wherein the amino group at the N-terminus is to the left and the carboxyl group at the C-terminus is to the right. Unless noted otherwise, all amino acids are L-amino acids.

Cyclophilin is a protein that has high affinity for the immunosuppressive drug cyclosporin A. Cyclosporin binding activity has been detected in animals, fungi, and plants, but is absent from bacteria (A. Koletsky et al., *J. of Immun.* 137:1054 (1986)). Recently the enzymatic activity of cyclophilin has been identified as peptidyl-prolyl cis-trans isomerase (N. Takahashi et al., (1989); G. Fischer et al., *Nature* 337:476 (1989)). Cyclophilin facilitates isomerization at proline residues in polypeptides. This activity has been hypothesized to be important in the folding of some proteins (G. Fischer et al., *Biochimica et Biophysics Acta* 829:39, (1985)) or in transduction of intracellular signals (G. Fischer et al., (1989)). In plants, the only nexus to cyclophilin is the detection of cyclosporin binding activity in extracts of zucchini (A. Koletsky et al., (1986)).

While cyclosporin binding activity has been detected in plants it has not been demonstrated that this activity derives from a cyclophilin gene. Such paucity of information on the role that cyclophilin plays in plant cells, coupled with the loosely defined role that cyclophilin plays in animal cells made the discovery that cyclophilin genes of plants express at high levels in essentially all plant cells unexpected. Prior to the present invention and demonstration that one of the highly expressed genes in plant cells encodes a plant cyclophilin, it would not have been possible to predict the desirable properties of a promoter of the plant cyclophilin gene. Until the isolation of the plant cyclophilin promoter, one would not have known that a plant cyclophilin promoter would express at high levels in essentially all cells.

Cloning vectors and expression vectors are taught herein in which a chimeric gene comprising a plant promoter region of a gene homologous to a cyclophilin gene probe is operatively linked to a structural protein coding sequence such that the operative in linking results in the coding region being transcribed when the vector is introduced into a plant or plant cells. For purposes of this invention, a chimeric gene comprises a plant cyclophilin promoter operatively linked to a structural coding sequence different from the naturally occurring cyclophilin coding sequence associated with the cyclophilin promoter. Likewise, heterologous with respect to the promoter means that the coding sequence does not exist in nature in the same gene with the promoter. However, the promoters of the invention may be modified to alter their expression characteristics. For example, the cauliflower mosaic virus 35S promoter may be ligated to the portion of the ssRUBISCO gene which represses the expression of ssRUBISCO in the absence of light, thereby creating a promoter which is active in leaves but not in roots. Similar modifications to plant cyclophilin promoters are contemplated herein.

Typically, the isolation procedure for a cyclophilin promoter is the same as for any other promoter. Therefore, the general procedure involves first obtaining cDNA for the desired gene containing the promoter, secondly, a genomic clone containing the desired gene is isolated, and thirdly, the desired promoter region is identified and isolated.

Generally, a cDNA library is constructed from polyA$^+$ RNA isolated from a collection of plant tissue. First, the total RNA is isolated followed by isolating polyA$^+$RNA from the total RNA. Double stranded cDNA can be synthesized from the isolated PolyA$^+$RNA. After ligation of linkers or adapters onto the cDNA, the cDNA is digested, size fractionated and separated by electrophoresis. The cDNA of desired length (greater than 400 base pairs (bp), for example, for cyclophilin) is extracted from the gel and ligated into a cDNA cloning vector and packaged into phage particles or is directly transformed into bacteria.

The initial cDNA can be isolated by a general screening procedure designed to identify cDNA clones deriving from highly expressed genes. In this method plaques are screened with labelled single stranded cDNA probes made from the polyA$^+$RNA from the target tissues as disclosed by C. Gasser et al. *Plant Cell* 1:15 (1989). Filters are eluted and probed with total genomic DNA (labelled by the random oligonucleotide priming method as disclosed in Feinberg et al., *Anal. Biochem.* 132:6 (1983)). DNA is isolated from clones which hybridize strongly to the first probe and weakly to the second probe. The DNA is digested with an appropriate restriction enzyme according to the linkers used in construction of the cDNA library to release inserts of desired sizes, for example cyclophilin inserts range in size from 250 base pairs (bp) to approximately 800 bp.

A genomic library can be constructed from genomic DNA which has been purified and partially digested or sheared to obtain the desired fragment lengths, for example 12 kb to 24 kb length fragments for cyclophilin. The fragments are then ligated into a cloning vector and amplified. The amplified library is then screened with the labelled desired gene probe. The promoter region is then identified as that set of sequences upstream of the desired gene coding sequence. A fragment of this region, for example a 1 kb to 4 kb fragment for cyclophilin, is then subcloned and engineered to allow attachment to other coding sequences and an appropriate 3'-sequence.

For some applications it might be desirable to use a promoter fragment less than an initially isolated fragment size. The minimal length of a promoter fragment can be determined by systematically removing sequences from the 5' and 3'-ends of the promoter region by standard techniques known to those skilled in the art of molecular biology including, but not limited to removal of restriction enzyme fragments or digestion with nucleases. The truncated promoter fragments can then be fused to a suitable reporter gene such as the *E. coli* β-glucuronidase gene (R. Jefferson et al., *EMBO J.* 6:3901 (1987)) or the chloramphenicol acetyltransferase gene (this coding sequence can be isolated from the plasmid pBR325 available from the American Type Culture Collection (ATCC), Rockville, Md.). These plasmids can be assayed for their ability to produce the reporter enzyme when introduced into transgenic plants or plant cells. The shortest promoter fragment that produces enzymes in the same or higher levels in all tissues as the initial fragment would then serve as the minimal promoter. Similarly, if a promoter fragment that was isolated from a plant shows low levels of expression, additional fragments on the 5'-flanking side of the promoter fragment can be attached until sufficient expression is achieved.

In some plant species more than one cyclophilin gene may be present in the genome (See Example 3 on the isolation of maize cyclophilin genes). In this case it is desirable to isolate genomic clones of all of the genes and assay the promoter fragments as described above to determine which gene included the most effective promoter fragment.

The identification of plant cDNA clones for cyclophilin genes and the demonstration of a high degree of similarity to other cyclophilin genes enable an efficient method for the isolation of cyclophilin cDNAs, genomic clones, and promoters from other species. In many cases a direct screen for a genomic clone can be employed, but if the genome of a given organism is especially large it might be desirable to isolate a cDNA clone from the intended organism first, and use this as a probe on the genomic library.

To isolate cyclophilin promoters from other plant species a library of genomic fragments from the species of interest is constructed, and possibly a cDNA library constructed, by standard methods familiar to molecular biologists. The genomic or cDNA libraries, or both, are then screened with an appropriate cyclophilin probe. The coding region from a cyclophilin cDNA clone of a species that is closely related to the target organism would be the optimal probe. Alternatively, based on the degeneracy of the genetic code, the amino acid sequences of cyclophilin proteins can be used to determine a variety of DNA sequences capable of coding for a particular cyclophilin protein and probes can be made based on this information.

Preferably clones for cyclophilin from dicots are identified by screening with probes based on dicot cyclophilin DNA or protein sequences, and clones for cyclophilin from monocots are identified by screening with probes based on monocot cyclophilin DNA or protein sequences. Both monocot and dicot cyclophilin DNA and protein sequences are disclosed herein. Therefore, based on these sequences one can screen for clones of cyclophilin genes from any plant using probes based on the tomato or *Brassica napus* sequences to screen for clones from dicots, and using probes based on the maize sequences to screen for clones from monocots. For example, within the monocots, one preferably screens for maize cyclophilin genomic clones with a probe based on the disclosed maize cyclophilin cDNA or protein sequences. The optimal method would be to use a probe made from the entire maize cDNA coding sequence to screen for the maize genomic clone. However, clones from other monocots (for example, wheat) can be isolated by screening with probes made from the maize cDNA sequence. The maize cDNA probe could be used to first screen a wheat cDNA library for a cDNA to wheat Cyclophilin. This wheat cDNA clone could then be used to screen a wheat genomic library for a clone of a wheat cyclophilin gene. Alternatively a probe made from the maize cDNA clone could be used to directly screen a wheat genomic library for a clone of a wheat cyclophilin gene. The promoter for wheat cyclophilin would then be isolated from the wheat genomic clone according to the procedures described herein. Similarly a genomic clone for tomato cyclophilin can be isolated by screening a tomato genomic library with a probe made from the tomato cyclophilin cDNA sequence described herein. Clones for cyclophilin from any other dicot species can be isolated by screening with probes made from the tomato (or *Brassica napus*) cDNA sequences. It may, however, be desirable to use shorter probes which can easily be synthesized on commercially available machines (if sequences are available and cDNA clones cannot be readily obtained). In this case the optimal probe would be chosen from the region encoding one of the more highly conserved regions of the protein, for example the region encoding amino acids 32–47 of the *Brassica napus* cyclophilin protein. The probes would optimally be synthesized as a mixture of sequences to account for the different possible codons that could encode each amino acid in the desired species.

When using this procedure to find other cyclophilin genes, the probe used to hybridize other cyclophilin genes will vary. Therefore, hybridization, for purposes of this invention, is not limited to any particular cyclophilin nucleic acid strand used as a probe. Due to the discovery of the high identity found between plant cyclophilins, and due to the degeneracy of the genetic code, based on the cyclophilin amino acid sequence, a wide range of probes may be designed. As skilled artisans will recognize, small nucleic acid fragments of a desired nucleic acid target sequence will hybridize to the target and thereby identify the desired target sequence. Therefore, if one has the entire coding sequence for a cyclophilin gene, coding regions anywhere within the entire gene can be used to hybridize the full length gene. For example, as few as about 24 nucleotides from any region of a full length cyclophilin gene, the 5' end, the 3' end, or anywhere in between, may be used to hybridize other cyclophilin genes or clones of cyclophilin genes. For example, due to the high degree of homology found between the cyclophilin genes in plants, ranging from tomato to maize, a small fragment from any of these cyclophilin genes can be used to hybridize any other full length cyclophilin gene, from whatever source. If two such probes were appropriately chosen from opposite strands of the coding sequence then the polymerase chain reaction (H. Erlich, *PCR Technology, Principles and Applications for DNA Amplification,* (1989) Stockton Press, New York, N.Y.) can be used to isolate a fragment of the cDNA or genomic DNA that can then be used to isolate a clone of the cyclophilin gene and its promoter.

Cyclophilin cDNA sequences and amino acid sequences are disclosed for tomato, *Brassica napus,* and. maize (FIGS. 1 and 2). Cyclophilin promoters were isolated from maize and *Brassica napus.* Those skilled in the art will recognize that *Brassica napus* and maize represent extremes of the higher plant phylum coming from the two major phylogenetic groups, the monocots and the dicots. Therefore, in view of the disclosure contained herein with respect to the plant cyclophilin from these two plant species, identification and isolation of other plant cyclophilin promoters can be achieved. In addition, other DNA sequences encoding the amino acids of cyclophilin gene products may be found due to the degeneracy of the genetic code.

Those skilled in the art will recognize that numerous variations on the specifics of procedures for isolation of cyclophilin promoters from other species, are possible (as described above and enabled by the disclosure of the sequences of dicot and monocot cyclophilin cDNAs and genes). Following is an example of a detailed protocol that enables the identification and isolation of a cyclophilin promoter from any plant species.

Sample Detailed Protocol for Isolation of Cyclophilin Promoter from any Plant Species The first step in the isolation of a cyclophilin promoter from a species other than those described in the examples is to choose an appropriate sequence from among those described in FIG. 1. If the desired species is a member of the Solanaceae family then the tomato cDNA sequence is preferred. If the desired species is a member of the Brassicacea (Crucifereae) then the *Brassica napus* sequence is preferred. If the desired species is a docot, but is not a member of either of the above families then either the tomato or the *Brassica napus* sequences may be used. If the plant is a monocot then the maize sequence is preferred. The following series of steps is then followed to isolate a cyclophilin promoter from the desired plant species:

I. Southern Hybridization of Genomic DNA from a Chosen Plant Species with Cyclophilin cDNA The purpose of this step is to determine if a coding sequence of cyclophilin from the chosen plant species can be detected in genomic DNA by differential hybridization to the cyclophilin cDNA chosen from those shown in FIG. 1. If detection is not possible by this method, it will be necessary to identify and isolate a cDNA from the chosen species capable of hybridizing to the cyclophilin cDNA of FIG. 1 before a genomic clone can be identified. If detection can be accomplished from genomic DNA, one can skip step II (below) and directly screen a genomic library for a homologous coding sequence using the cyclophilin cDNA chosen from those shown in FIG. 1 as the probe. In this case, a second purpose of this step is to provide an estimate of the copy number of the isolated coding sequence in the chosen species.

A. Isolation of Genomic DNA

1. Collect about 1 gram (gm) of young leaf tissue.
2. Add 10 milliliters (mls) of extraction buffer and grind with a mortar and pestle until pasty. Extraction buffer comprises:
   50 mM Tris, pH8.0
   50 mM EDTA
   50 mM NaCl
   400 μg/ml Ethidium Bromide (EtBr)
   2% N-lauryl sarcosine (Sarkosyl)
3. Centrifuge (Cfg) for 30 minutes @ 12,000 g, 5° C. in a screwcap oakridge tube.
4. Add 0.95 gm CsCl per ml of supernatant.
5. Cfg 20 minutes @ 10,000 g, 5° C.
6. Remove supernatant and place into ultracentrifuge tubes.
7. Cfg 20–48 hours @ 44,000 rpm, 20° C., in a Beckman VTi80 rotor or the like.
8. DNA will appear as an UV fluorescent band in the tube. Extract band from tube using a needle and syringe and place into a clean tube.
9. Add 1 volume of isopropanol (saturated with 20X standard saline citrate (SSC)), mix, let settle, and then remove upper phase (which will contain red stain (EtBr)). Repeat extraction with saturated isopropanol until all red stain is removed from lower phase.
10. Add 2 volumes of cold ethanol to remaining clear lower phase and cfg @ 15,000 rpm in a microfuge for 5 minutes.
11. Remove supernatant, let pellet dry and then resuspend in 0.5 ml of TE buffer (10 mM Tris, pH 7.5, 1 mM EDTA).
12. Quantitate the DNA concentration by measuring the UV absorbance of an aliquot at 260 nm wavelength using a spectrophotometer. One O.D. unit of absorption at this wavelength represents 50 μg of DNA.

This procedure is sufficient for most plant species, but for those species that contain compounds that would hinder this procedure, alternate methodologies are available and known in the art.

B. Digestion and Electrophoresis of Genomic DNA

When the genomic DNA has been isolated, it is then digested separately with EcoRI, HindIII and BamHI restriction enzymes and electrophoresed on an agarose gel according to the following general protocol.

1. Add to a 1.5 ml eppendorf tube:
   10 μg of genomic DNA
   50 μl of 10×enzyme buffer (as suggested by enzyme supplier)
   5 μl of restriction enzyme (New England Biolabs)
   Add distilled water to bring volume to 500 μl.
   Incubate at 37° C. for 4 hours or more.
The DNA is digested separately with EcoRI, HindIII, and BamHI restriction enzymes.
2. Precipitate DNA by adding 50 μl of 3M Sodium Acetate and 1 ml of ethanol to each tube, chill on dry ice, and cfg @ 15,000 rpm for 5 minutes. Resuspend pellets in 20 μl of TE buffer.
3. Electrophorese digested genomic DNA (along with Lambda DNA cut with BstEII as a size standard) at 2V/cm for 3–4 hours through a gel containing:
   1% agarose
   1 μg/ml EtBr
   40 mM Tris-acetate pH7.5
   1 mM EDTA When gel is complete, take a picture of the gel under a UV light using an appropriate camera.

C. Immobilizing DNA Onto Nylon Membrane

1. Immerse the agarose gel in a 0.25M HCl solution for 20 minutes, then rinse gel with distilled water.
2. Immerse gel in denaturant (0.5N NaOH, 1.5M NaCl) for 1 hour, changing the solution once, then rinse with distilled water.
3. Immerse gel in neutralizer (0.5M Tris-Cl, pH7.0, 3M NaCl) for 1 hour, changing the solution once, then rinse with distilled water.
4. Place gel on Whatman 3MM paper (Chromatography paper) (Whatman International Limited, England) soaking in 10×SSC.
5. Place nylon hybridization membrane (Micron Separations Inc.) soaked in 10×SSC directly onto the surface of the gel. Place 2 sheets of Whatman 3MM paper on the membrane followed by a 10 cm stack of dry paper towels. (This will create a movement of 10×SSC through the gel and into the dry towels via capillary action). The DNA in the agarose gel is also moving onto the nylon hybridization membrane. Continue this for at least 10 hours.
6. Remove membrane from gel, rinse in 10×SSC, and bake membrane at 80° C. for 2 hours.

D. Radiolabelling the Isolated Cyclophilin cDNA Coding Sequence

Labelling of the cDNA with a radioactive deoxynucleotide(s) can be accomplished by an oligolabelling procedure (A. Feinberg et al., *Anal. Biochem.,*132:6 (1983)) or by any other preferred method. The oligolabelling procedure described below uses a kit supplied by Pharmacia. The labelled cDNA should be used for hybridization (step E, below) within a few days after it has been made.

1. Boil 50 ng of purified insert cDNA clone from the chosen clyclophilin in a 1.5 ml tube for 8 minutes, place on ice 1 minute.
2. At 25° C. add to DNA:
   10 μl reagent mix
   2 μl BSA (bovine serum albumin)
   5 μl (50 μCi) $^{32}$P dCTP (3000 Ci/mmole)
   2 μl Klenow Polymerase
   Add distilled water to 50 μl final volume.
   Incubate overnight at room temperature.
Reagent mix (pH8.0) contains:
   100 μM DATP
   100 μM dGTP
   100 μM dTTP
   250 mM Tris-HCl (pH8.0)
   25 mM magnesium chloride
   50 mM 2-mercaptoethanol
   90 O.D. units/ml random hexanucleotide oligomers
3. Add 50 μl of stop solution (contains cytidine 5'-triphosphate (dCTP), ethylenediamine tetraacetic acid (EDTA), sodium dodecyl sulphate (SDS), NaCl, and buffer).
4. Purify labelled cDNA from unincorporated $^{32}$P dCTP by passing it through a Sephadex G-50 DNA grade spin column (Boehringer-Mannheim, Indianapolis, Ind.) according to the manufacturer's instructions or, alternatively, a Sephadex column can be made in a 5 ml disposable pipette. The labelled cDNA will pass through the column more quickly than the free nucleotide and can thus be separated by collecting the appropriate fraction that elutes from the column. Quantitate the amount of incorporated $^{32}P$ dCTP by counting 1 μl of the labelled cDNA using a scintillation counter. The total labelled cDNA should contain at least 50 million cpm (counts per minute) for every 50 ng of DNA used.

E. Hybridizing the Labelled Cyclophilin cDNA Coding Sequence to Immobilized Genomic DNA 1. Place nylon hybridization membrane in a bag containing enough hybridization solution for total immersion, seal, and incubate at 45° C. for at least 2 hours.

Hybridization solution contains:
6×SSC
0.01 M EDTA
5×Denhardt's Solution (1 mg/ml of Ficoll, BSA, and polyvinylpyrrolidone)
100 μg/ml denatured salmon sperm DNA 0.5% SDS 2. Boil the labelled cDNA from step D, above, for 8 minutes.

3. Add the labelled cDNA to the bag containing the membrane immersed in hybridization solution, reseal. For every milliliter of hybridization solution, 1 million cpm of the labelled cDNA should be added. Incubate bag at 45° C. for 24–48 hours.

4. Remove membrane from bag and submerge in a wash solution containing 6×SSC, 0.2% SDS. Incubate at 45° C. for 30 minutes.

5. Measure radioactivity on the membrane using a geiger counter. If parts of the membrane which contain no DNA contain greater than 0.2 mREM/lhr of radioactivity, wash the membrane for another 30 minutes with 6×SSC, 0.2% SDS. If a significant background radioactivity persists, begin washing the membrane with wash solution containing decreasing amounts of SSC (from 6×to 5× to 4×, etc.) while continuing to check the background radioactivity at 30 minute intervals.

6. As soon as the background radioactivity on the membrane is below 0.2 mREM/hr, enclose it in plastic wrap to keep it moist. Then expose a piece of X-ray film to the membrane at −80° C. in complete darkness. Develop the film after 24 hours. If no hybridization to the immobilized DNA can be seen (successful hybridization appears as dark bands on the film) a longer exposure (up to 2 weeks) will be necessary. If too much hybridization is seen (as a dark smear over the immobilized DNA instead of discrete bands) then a shorter exposure should be done. If reduction in exposure time does not eliminate the problem, it will be necessary to wash the membrane in lower amounts of SSC following the procedure in step 5 above, and then re-exposing X-ray film to the membrane.

If discrete bands can be detected on the X-ray film, the cyclophilin cDNA selected from FIG. 1 can be used to directly identify a genomic clone from the chosen species containing a coding sequence homologous to the isolated cyclophilin cDNA coding sequence, and step II, below, can be skipped. The number of digested DNA bands which hybridize to the cyclophilin cDNA provides an indication of the copy number of the homologous coding sequence in this species. If 1–2 bands of DNA digested with EcoRI, HindIII, or BamHI hybridizes to the cyclophilin cDNA, it is likely that the copy number of the homologous coding sequence in the chosen species is low (1–3 copies). Multiple hybridizing bands indicate a proportional increase in the copy number estimate.

II. Identification and Isolation of a Cyclophilin cDNA from the Chosen Species p The purpose of this step is to obtain a clone of a cyclophilin cDNA from the plant species of choice. This cDNA can be used to identify a cyclophilin gene (including the promoter associated with the coding sequence) that is expressed in essentially all tissues of the chosen species in step III, below.

A. Isolation of RNA

The tissue chosen should be as enriched as possible in small cells with minimal vacuoles. For most plant species young floral buds should suffice. The yield of RNA will vary but a sufficient quantity should be obtained from 10 grams of starting tissue.

The following solutions should be prepared:

Lysis buffer: Make up fresh and filter sterilize before each use, add first two components as powder, others from concentrated stocks.

1% Tri-iso-propylnapthalenesulfonic acid ammonium salt (SP/Kodak)
6% p-Aminosalicylic acid
100 mM Tris-HCl, pH 7.6
50 mM ethyleneglycobis (β-aminoethyl) ether tretraacetic acid (EGTA), pH8.0
100 mM NaCl
1% SDS
50 mM 2-mercaptoethanol PCI: (phenol, chloroform, isoamyl) Combine equal volumes of chloroform:isoamyl alcohol (24:1) and tris saturated phenol.

When making up the buffer and reagents it is necessary to use autoclaved or diethylpyrocarbonate (DEPC) treated autoclaved water.

1. Freeze tissue in liquid nitrogen and grind in a mortar and pestle to a very fine powder.

2. Add the frozen powder to lysis buffer and PCI. Use 3–5 ml of buffer per gram of tissue and an equal volume of PCI.

3. Homogenize immediately with a polytron tissue distruptor or the like.

4. Cfg. @ room temperature, 12,000 g for 5 minutes to separate phases. Re-extract the aqueous phase with an equal volume of PCI and save the aqueous phase.

5. Add one tenth volume of 3M Sodium Acetate (Na Acetate) and 2.5 volumes of ethanol to aqueous phase, mix. Store at −20° C. overnight or until frozen at −80° C.

6. Cfg@ 12,000 g for 25 minutes to sediment precipitate. Pour off supernatant.

7. Dissolve the pellet in water, using one half of the original lysis volume. When the pellet is in solution add an equal volume of cold 4M lithium chloride (LiCl). Place on ice at least 2 hours.

8. Cfg @ 4° C., 12,000 g for 25 minutes.

9. Remove supernatant with care (to avoid loss of the transparent RNA pellet). Allow tube to drain for 10 minutes.

10. Add one fourth of the original volume of water to dissolve the pellet. Then add an equal volume of cold 4M LiCl. Store on ice for at least 1 hour.

11. Repeat steps 8–10 above.

12. Repeat steps 8 and 9 again. Dissolve RNA in 0.9 ml of sterile water. Add 100 μl of 3M Na Acetate and 2.5 ml of ethanol.

Store at −20° C. for at least 2 hours.

13. Cfg in microfuge tubes @ 15,000 rpm, 4° C. for 15 minutes. Remove supernatant and allow pellets to air dry for 5–10 minutes. Resuspend in 0.5–1 ml of sterile water.

14. Isolate the polyA+ RNA from the total RNA using a poly(A) quick column (Stratagene) or the like according to the manufacturer's instructions.

15. Quantitate the RNA concentration by measuring the UV absorbance of an aliquot at 260 nm wavelength using a spectrophotometer. One O.D. unit of absorption at this wavelength represents 40 μg of RNA.

B. Making a cDNA Library from RNA

1. First strand synthesis: Ten μl of Actinomycin D (400 μg/ml, Sigma) in 50% Ethanol (EtOH) is dried down in each reaction tube in a Savant speed vac. The following reagents are added to this tube (in the order given):

| Vol. | Substance | Final Conc. or Amount |
|---|---|---|
| 62 μl | Autoclaved Water (no DEPC) | |
| 10 μl | 10 X first strand buffer (see below) | 1 X |
| 10 μl | 5 mM dNTP | 500 μM each A, C, G, T (Sigma) |
| 10 μl | 100 μg/ml oligo d(pT) | 1 μg (Collaborative Research) |
| 2 μl | RNAsin (30 U/μl) (Promega) | 60 U |
| 2 μl | RNA | 1.5 μg |
| 2 μl | Reverse Transcriptase | 40 units (Life Sciences Corp., St. Petersburg, FL) |
| 2 μl | 32P-dATP | 200 Ci/mMole (Amersham Corp.) |

The reaction is incubated @ 42° C. for 60 minutes, then frozen on dry ice and stored at −20° C.

10×First strand buffer consists of:

500 mM Tris-HCl, pH 8.3

300 mM KCl 100 mM MgCl$_2$ 4 mM dithiothreitol (DTT)

The quantity of cDNA synthesized is determined by precipitation of a portion of the reaction with trichloroacetic acid and scintillation counting.

2. Purification of the first strand:

Biogel P60 (100–200 mesh, Bio Rad, Richmond, Calif.) pre-swollen in 10 mM Tris-HCl/1 mM EDTA, pH8.0 (TE buffer) is used to pour a column in a siliconized pasteur pipet plugged with siliconized glass wool (bed volume=1 ml). Wash the column with several volumes of 1 mM Tris pH 7.6/0.01 mM EDTA. Calibrate the column by running 90 μl of this same solution+10 μl column marker buffer (Column Marker buffer comprises: 5% Blue Dextran (2M dalton, Sigma) and 0.05% Phenol Red (or Bromphenol Blue at 0.1%) dissolved in 10 mM Tris, pH7–8, 1 mM EDTA) over the column, noting when the blue dextran is eluted. Add more buffer to the column to elute the red dye.

Extract the first strand reaction twice with an equal volume of phenol. Add 0.5 μl of 2% bromphenol blue to the cDNA and load it on the column. Collect drops at the same time as the blue dextran eluted during calibration. The volume collected should be 250–300 μl.

3. Second strand synthesis and methylation

Dry the first strand to about 10 μl in vacuo.

Then add the following:

| Vol. | Substance | Final Conc. or Amount |
|---|---|---|
| 10 μl | cDNA | 700 ng or less |
| 10 μl | 10 X second strand buffer | 1 X |
| 0.8 μl | 5 mM dNTP (N=A, G, C, T) | 40 μM each |
| 2 μl | E. coli DNA PolI (NEB) | 20 units |
| 0.4 μl | E. coli DNA ligase (NEB) | 2 units |
| 0.5 μl | RNAase H (BRL) | 1 unit |

-continued

| Vol. | Substance | Final Conc. or Amount |
|---|---|---|
| 1 μl | BSA (BRL) | 50 μg/ml |
| — | water to 100 μl final volume | |
| 3 μl | 32P dCTP (optional) | 30 μCi |

NEB = New England Biolabs, Beverly, MA; BRL = Bethesda Research Labs, Gaithersberg, MD.

Incubate the reaction at 14° C. for 60 minutes, then at room temperature for 60 minutes.

10×Second Strand Buffer contains:

200 mMTris-Cl pH 7.4–7.5

50 mM MgCl$_2$ 1.0 M KCl 100 mM Ammonium Sulfate 1.5 mM Beta-NAD

Add:

0.5 μl of 5 mM dNTP

1 μl of T4 DNA polymerase (NEB)

Incubate the reaction for 30 minutes at room temperature. Then add:

1.2 μl of 1 mM S-adenosyl L-methionine (Sigma)

1.0 μl of Eco RI Methylase (NEB)

2.4 μl of 0.5 M EDTA

Remove 5 μl from the reaction and add to 260 ng wild type lambda DNA (NEB) as a test reaction for methylation.

Incubate at 37° C. for 45 minutes.

Heat both the main and test reactions to 68° C. for 10 minutes to inactivate enzymes.

4. Assay for completeness of methylation

To the heat treated test methylation add:

2 μl of high salt restriction buffer

12 μl of water

1 μl of EcoRI (20 units BRL)

0.5 μl of pUC 19 DNA (0.5 μg)

High salt restriction buffer=100 mM Tris-HCl, pH7.6

100 mM MgCl$_2$ 1.0 M NaCl

Incubate for 1 hour at 37° C.

Run on a 1% agarose gel along with 1 μg of undigested pUC19 DNA and lambda DNA digested with BstEII (NEB size markers). The pUC19 DNA in the reaction should be completely digested and the lambda DNA in the test reaction should be completely undigested. This shows that the methylase is effective in blocking the EcoRI sites in the cDNA from digestion.

5. Clean up double stranded cDNA

Extract the second strand reaction mixture twice with an equal volume of phenol. Add 0.5 μl of 0.2% bromphenol blue and run over a P60 column as above (see step 1, first strand synthesis) and dry to less than 5 μl in a speed vac.

6. Ligation of linkers to the cDNA

In a microfuge tube mix:

-- μl of dscDNA (up to 5 μl or 500 ng)

2.5 μl of Phosphorylated Eco RI linkers (NEB, 250 ng)

1 μl of 10×Ligation buffer

1 μl of 10 mM ATP

-- μl of water (for final vol of 10 μl)

1 μl of T4 DNA Ligase (~400 units NEB)

Incubate at 14° C. for 12 hours.

10×Ligation buffer:

300 mM Tris-Cl, pH7.6

100 mM MgCl$_2$ 50 mM DTT

7. Removal of linkers

Add to the ligation mix solution of #6, above:

2 μl of high salt restriction buffer

6 μl of water

Heat to 68° C. for 10 minutes to inactivate ligase. Then add:

2 μl of EcoRI (40 units, NEB)

Incubate at 37° C. for 2.5 hours.

Then heat to 68° C. for 10 minutes to inactivate EcoRI.

8. Separate the cDNA from the linkers and purify

Add 5 μl of loading buffer to the digested cDNA/EcoRI linker reaction. Then electrophorese on a 0.8% Sea Plaque agarose (FMC Corp. Rockland, Md.)/TEA (40 mM Tris-Acetate/1.6 mM EDTA) minigel containing 0.3 μg/ml ethidium bromide. Run the gel at 4 V/cm until the bromphenol blue dye has migrated 4 centimeters. Lambda DNA digested with Hind III and EcoRI is also loaded onto the gel as a size marker. After electrophoresis the markers are visualized by UV fluorescence.

Loading Buffer contains:

250 mM of EDTA pH7

0.2% of Bromphenol blue

50% of Glycerol

Recover the cDNA from the gel using a diethylaminoethyl (DEAE) membrane (NA45, available from Schleicher and Schuell). Pretreat membrane by the following method:

Place DEAE membrane in 10 mM Tris pH7.6/10 mM EDTA for 10 minutes and then in 0.5 M NaOH for 5 minutes. Rinse with distilled water and store (indefinitely) at 4° C. in 10 mM EDTA, pH~7.5.

When the gel has run far enough (until Bromphenol Blue dye has run 4 cm) make a slit in the gel lane containing the cDNA sample at the lowest molecular weight required (500 bp) based on migration of the size markers in adjacent lanes and insert a piece of the DEAE membrane that is just slightly wider than the gel lane. Electrophorese the cDNA into the membrane. Remove the membrane from the gel. The area that has bound cDNA can be visualized by UV fluorescence due to the ethidium bromide in the gel. Trim away as much membrane as possible that does not have cDNA bound to it. Wash the membrane two times for 5 minutes in 5 millimeters of:

150 mM NaCl 20 mM Tris pH8.0

0.1 mM ELTA

Transfer to a microfuge tube and add 500 μl of:

1.0 M NaCl 20 mM Tris pH8.0

0.1 mM EDTA and heat to 55° C. for 25 minutes. Remove the supernatant which now contains about 70% of the cDNA. The rest is lost on the membrane. Spin the tube for 5 minutes in a microfuge to remove any possible traces of membrane pieces and transfer the supernatant to a clean tube.

9. Ligation of cDNA to lambda ZAP or equivalent

Add 2 μl (2 μg) of lambda ZAP arms (lambda Zap DNA treated with EcoRI and Alkaline phosphatase, Stratagene) or an equivalent to the cDNA. The lambda ZAP arms contain the pBluescript sequences. Then add 1 ml of cold EtOH and chill at −80° C. for 1 hour. Centrifuge at 15,000 rpm for 15 minutes. Drain the tube and wipe out the inside with a sterile swab carefully avoiding the pellet (which may be invisible). Rinse with 200 μl of 70% ethanol chilled to −20° C. without disturbing the pellet. Let the pellet air dry for about 30 minutes.

Add to the dried pellet:

7.2 μl of Water

1 μl of 10×Ligation Buffer

1 μl of 10 mM ATP 0.8 μl T4 DNA Ligase

Incubate 20 hours at 14° C.

10×Ligation Buffer comprises:

200 mM Tris-HCl, pH7.6

100 Mm MgCl$_2$ 50 mM DTT

10. Packaging ligated cDNA

The cDNA is now ready for packaging and plating into bacteriophage. Package one fourth (2.5 μl) of the ligation reaction in vitro into phage using Gigapack packaging extracts (Stratagene Cloning Systems, San Diego, Calif.) or an equivalent according to the manufacturer's instructions.

11. Plating the packaged cDNA

Grow 2 ml of E.coli strain BB4 (Stratagene) in TB media* supplemented with 0.2% maltose and 10 mM magnesium sulfate to an O.D.600 of 0.5. Transfer 600 μl to a 10 ml tube and add 1 μl of the packaged cDNA. Incubate for 15 minutes at 37° C. while gently shaking. Then add 4 ml of melted top agar (48° C.), 50 μl of 0.5M isopropylthiogalactoside (IPTG), and 50 μl of 250 mg/ml 5-bromo-4-chloro-3-indolyl-β-D-galactoside (X-Gal.). Pour immediately and evenly onto a 15 cm NZY agar plate. Incubate at 37° C. After 6 hours plaques should be visible. White plaques represent packaged cDNA's and should be 10–100 fold more abundant than blue plaques representing lambda-ZAP containing no cDNA insert. Calculate the number of plaque forming units (PFU) per μl of the cDNA library for future plating.

*TB media:

5 g/l NaCl 10 g/l Bacto-tryptone

Dissolve in water; autoclave to sterilize.

NZY plates:

5 g/l NaCl 2 g/l hydrated magnesium sulfate 5 g/l yeast extract 10 g/l NZ Amine (casein hydrolysate)

15 g/l Difco agar

Dissolve in water, autoclave to sterilize.

Pour about 80 ml/15 cm plate. Allow plates to dry 15 minutes (without lids) in a laminar flow hood prior to use.

Top agar:

Same as NZY plates but substitute agar with 0.7% agarose. Cool to 48° C. before use.

C. Identification of a DNA Coding Sequence from the Chosen Species Homologous to the Isolated Cyclophilin cDNA Coding Sequence 1. Immobilizing cDNA onto nitrocellulose Using the procedure described above, step B-10, make 10 plates (15 cm) with about 15,000 cDNA plaques per plate. Incubate plates until plaques are clearly visible (8 hours). Then for each plate place a nitrocellulose filter (cut to the plate's form) in contact with the top agar for 1 minute. Make corresponding marks on each filter and plate so that filters can later be realigned to the plates in the same configuration. Remove the filters carefully (avoid disturbing top agar) and immerse them in denaturant (0.1N NaOH, 1.5M NaCl). After 3 minutes transfer the filters to neutralizer solution (0.2M Tris-HCl, pH7.6/2×SSC) for 5 minutes. Rinse filters after neutralization in 2×SSC and place on Whatman 3MM paper to air dry for 5 minutes. Next wrap filters in between sheets of Whatman filter paper and bake for 2 hours at 80° C. in vacuuo. Duplicate filters can be made for each plate as well by repeating the procedure above with the exception that the filters are left in contact with the top agar for 3 minutes instead of 1 minute.

2. Hybridizing the cDNA library of the chosen plant species to cyclophilin cDNA

Make a radiolabelled cyclophilin cDNA according to the protocol described in step I-D, above. Place filters in a sealable bag and add just enough hybridization buffer to completely immerse them. Seal the bag and incubate at 45° C. for at least 4 hours. Boil a mixture of 1 million counts of labelled cyclophilin cDNA and 100 ng of pBluescript that has been digested with EcoRI for each ml of hybridization mix for 8 minutes. Add this mixture to the hybridization mix and incubate for 24–48 hours at 45° C.

Remove the filters from the bags and submerge in wash solution containing 6×SSC, 0.2% SDS. Incubate at 45° C. for 30 minutes. After this incubation measure the radioactivity remaining on the filters using a geiger counter. If there is a general level of radioactivity across each filter that is greater than 0.2 nREM/hr, wash the filters for another 30 minutes with 6×SSC, 0.2% SDS. If the radioactivity across each filter is still greater than 0.2mREM/hr begin washing the filters with wash solution containing decreasing amounts of SSC (from 6× to 5× to 4×, etc.) while continuing to check radioactivity at 30 minute intervals.

When the radioactivity across the filters falls below 0.2 mREM/hr, enclose them in plastic wrap and keep moist. Then expose a piece of X-ray film to the filters at −80° C. in complete darkness. After a 24 hour exposure, develop the film. Before removing the film from contact with the filters, mark the film so that it can be realigned with the filters after developing. If no hybridization is apparent a longer exposure (up to 2 weeks) will be necessary. If too much hybridization is seen (as dark staining across the whole filter area) then a shorter exposure should be done. If reduction in exposure time does not eliminate the problem, it will be necessary to wash the filters in lower amounts of SSC as described in the previous paragraph and then re-exposing them to X-ray film.

These adjustments should result in the visualization of dark spots on the X-ray film corresponding to cDNA from individual plaque(s) on the filter. These dark spots represent specific hybridization of the cyclophilin cDNA to a plaque (s) containing a homologous cDNA from the chosen species. Using the alignment marks, it is possible to identify the intact plaques on the original plates corresponding to cDNA hybridization. These plaques are removed from the plates with the small end of a pasteur pipette and placed into a microfuge tube containing 1 ml of SM buffer*. The phage are eluted from the agar into the SM by incubation for 2 hours at room temp. The eluted phage are probably not completely pure at this stage, containing contaminating phage that were adjacent to the target phage (containing the cDNA) on the plate.

In order to further purify the phage containing the cDNA, another round of plating/hybridization is performed. Following the procedure in B-10 and C, above, each eluted phage is plated on a single plate at a low concentration (100–1000 plaques/15 cm plate), filters are made, and hybridized to the cyclophilin cDNA in order to identify well separated plaques containing homologous cDNAs. One well isolated plaque from each plate is removed and eluted into 1 ml of SM buffer as above. This eluted phage should be pure enough to proceed to the next cloning step. An aliquot (5–10 μl) should be plated in order to quantitate the number of plaque forming units(pfu) per microliter.

*SM buffer:
5.8 g/lNaCl
2.0 g/l magnesium sulfate
50 ml 1M Tris-HCl, pH7.5
5 ml 2% gelatin
Dissolve in water, autoclave to sterilize.

D. Transfer of the Cloned cDNA Into *E. coli*

1. In a 50 ml conical tube combine:
   200 μl of *E.coli* strain XL1-Blue (Stratagene) cells grown in TB media to OD600=1.0
   200 μl of purified, eluted phage from previous step which should contain at least 100,000 pfu
   10 μl of VCS M13 (obtained from Stratagene Inc.) helper phage containing at least 10,000 pfu
   Incubate at 37° C. for 15 minutes.

2. Add 5 ml of 2XYT media and incubate 4–6 hours at 37° C. with shaking.
   2XYT media comprises: 5 g/l NaCL, 10 g/l yeast extract and 16 g/l Bacto-tryptone.

3. Heat tube at 70° C. for 20 minutes, then spin tube for 5 minutes at 1000 g. Transfer supernatant to a sterile tube. This supernatant contains the packaged pBluescript plasmid with cDNA insert in M13 or f1 phage particles.

4. Combine the following in two tubes:
   200 μl of *E.coli* strain XL1-Blue cells grown in TB media to OD600=1.0
   200 μl of phage stock from step 3 above (tube 1) or
   2 μl of phage stock from step 3 (tube 2)
   Incubate tubes at 37° C. for 15 minutes.

5. Plate 50 μl from each tube onto L-broth plates containing 200 μg/ml of Ampicillin. Incubate overnight at 37° C. Colonies appearing on the plates should contain the pBluescript plasmid with the cDNA insert. Pick a well separated colony with a sterile toothpick and transfer to a tube containing 2 ml of L-broth and 200 μg/ml ampicillin. Incubate at 37° C. while shaking until the culture is saturated (6–12 hours). Then combine 1 ml of the culture and 1 ml of sterile glycerol in a screwcap glass vial, mix, and freeze at −80° C. This can serve as a stock culture of the homologous cDNA from the chosen plant species in *E.coli*.

L-broth contains:
10 g/l Bacto-tryptone
5 g/l yeast extract
5 g/l NaCl

E. Characterization of the cDNA Insert from *E. coli*

1. Isolate plasmid DNA

Grow a 2 ml culture of *E. coli* containing the pBluescript plasmid with the cDNA insert in L-broth+200 μg/ml ampicillin from a stock.

Incubate at 37° C. while shaking until the culture is saturated (overnight). Then transfer 1.5 ml of culture to a microfuge tube and cfg for 15 seconds to pellet cells. Pour off the supernatant and resuspend the cell pellet in 100 μl of solution 1. Add 200 μl of solution 2, mix, and incubate on ice for 5 minutes. Then add 150 μl of solution 3, mix, and incubate on ice for 30 minutes. Cfg for 5 minutes. Transfer supernatant to a clean tube containing 0.5 ml of Tris-saturated phenol, mix. Cfg for 5 minutes. Carefully remove upper phase and transfer to a microfuge tube containing 1 ml of ethanol and incubate on dry ice for 30 minutes. Cfg for 5 minutes to pellet DNA. Remove supernatant and let pellet air dry. Dissolve pellet in 50 µl of water+1 µl of RNase (0.1 mg/ml). This plasmid DNA should be at a concentration of about 0.2 µg/µl.

Solution 1:
50 mM glucose
10 mM EDTA
25 mM Tris-HCl (pH8.0)
Solution 2:
0.2N NaOH
1% SDS
Solution 3:
3M potassium acetate
115 µl/ml of glacial acetic acid 2. Restriction mapping of the cDNA insert Digest the plasmid DNA with several restriction enzymes including EcoRI, HindIII, BamHI, PsttI, and XbaI under conditions supplied by the manufacturer. Each digest should include 5 µl of plasmid DNA and 10 µl total volume. Add 1 µl of loading buffer to each digested DNA and electrophorese on a 0.8% agarose/TEA (40 mM Tris acetate, 1.6 mM EDTA) minigel containing 0.3 µg/ml ethidium bromide. Lambda DNA digested with BstEII is co-electrophoresed as a size marker. Run the gel at 4 V/cm until the bromphenol blue has migrated 7 cm. Visualize the DNA bands under UV fluorescence and photograph. The size of the digested DNA fragments can be determined by comparison with the known sizes of the digested lambda DNA fragments. The size of the cDNA insert and the location of restriction sites within it can be determined by comparing the sizes of the restriction fragments with the known restriction map of the pBluescript plasmid.

The size of the cDNA insert should be at least 500 bp. If it is smaller, a larger insert containing the majority of the cDNA should be isolated.

3. Sequencing of the cyclophilin cDNA from the chosen species

The plasmid DNA can be sequenced by the dideoxy method of F. Sanger et al. *Proc. Natl. Acad. Sci. USA*, 74:5463 (1977), using a sequencing kit available from U.S. Biochem. Co. according to the manufacturer's instructions or by any method of preference. Sequencing with the M13 −20 primer (Stratagene) will provide sequence of either the 5' or 3' end of the cDNA, depending on its orientation in the pBluescript plasmid. Repeat the sequencing using the reverse primer (Stratagene) to obtain the sequence of the other end. Determine sufficient sequence from each end so that the sequence of the entire clone is determined. The sequence of the new cDNA clone should then be compared to the sequence of the cyclophilin cDNA used as a probe in its isolation (chosen from those in FIG. 1). If the newly isolated cDNA clone contains an open reading frame that has more than about 70% identity with the protein coding region of the probe sequence then it represents a cyclophilin cDNA from the chosen species. If the clone does not contain such a region, then it represents a spuriously isolated clone and additional clones should be isolated as described and sequenced until one matching these criteria is isolated. The sequence homology will additionally indicate the 5' and 3' ends of the cDNA clone.

Once the cDNA insert has been oriented, a restriction fragment observed in step 2, above, between 300 and 500 bp encompassing the 5' end should be identified. If such a fragment does not exist, further restriction mapping using other enzymes should be performed until one is identified. This fragment will be suitable for isolating and radiolabelling to probe for the promoter of the cyclophilin gene(s) in the genome of the chosen plant species (step III).

III. Identification and Isolation of the Promoter of the Corresponding Cyclophilin Gene from the Genome of the Chosen Species A. Making a Library of Genomic Fragments Cloned Into Phage 1. Perform a partial digestion of genomic DNA with MboI:

To a microfuge tube add:
 10 µg of genomic DNA of chosen species (see I-A)
 10 µl of 10×enzyme buffer (as suggested by enzyme supplier)
 10 units of MboI restriction enzyme (New England Biolabs)

Add water to final volume of 100 µl. Incubate tube at 37° C. At 1 minute intervals transfer a 10 µl aliquot of the reaction mix to a clean tube, add 1 µl loading buffer, and place on ice. After all of the reaction mix has been aliquoted and put on ice, load all the aliquots onto a 0.8% agarose gel along with 1 µg of lambda DNA digested with 1) BstEII and 2) HindIII and electrophorese at 4 V/cm until the bromphenol blue dye has migrated about 6 cm. Then visualize the DNA by observing the gel under UV light. Using the digested lambda DNA as size markers, determine which aliquot contains the most genomic DNA between 14 and 23 kb. This aliquot represents the optimal partial digestion time.

2. Isolate partial MboI digested genomic DNA

To a microfuge tube add:
 25 µg of genomic DNA of chosen species (see I-A)
 25 µl of 10×enzyme buffer (suggested by enzyme supplier)
 25 units of MboI restriction enzyme (New England Biolabs)

Add water to final volume of 250 µl. Incubate tube at 37° C. for the optimal partial digestion time (see above). Add 25 µl of loading buffer and load onto a 0.8% agarose gel with lambda size markers and electrophorese as described in step 1, supra. When the gel has run far enough (until the Bromphenol Blue dye has run at least 6 cm) make a slit in the gel lane(s) containing the genomic DNA sample at the lowest molecular weight required (14 kb) based on migration of the size markers in adjacent lanes and insert a piece of pretreated DEAE membrane (NA45, see step IIB-8) that encompasses the gel lane(s). Electrophorese the DNA into the membrane until the 23 kb lambda HindIII marker is adjacent to the membrane. Remove the membrane from the gel. The area that has bound DNA can be visualized by UV fluorescence due to the ethidium bromide in the gel. Trim away as much membrane as possible that does not have DNA bound to it. Wash the membrane twice for 5 minutes in 5 ml of:

150 mM NaCl
20 mM Tris pH8.0
0.1 mM EDTA

Transfer to a microfuge tube and add 500 µl of:

1.0 M NaCl
20 mM Tris pH8.0
0.1 mM EDTA

Heat to 55° C. for 25 minutes. Remove the supernatant which now contains about 70% of the DNA. The rest is lost on the membrane. Spin the tube for 5 minutes in a microfuge to remove any possible traces of membrane pieces and transfer the supernatant to a clean tube.

Add 2 μl (2 μg) of lambda EMBL3 phage arms (EMBL3 digested with BamHI and EcoRI, from Stratagene) or an equivalent to the tube. Then add 1 ml of cold EtOH and chill at −80° C. for 1 hour. Centrifuge at 15,000 rpm for 15 minutes. Drain the tube and wipe out the inside with a sterile swab carefully avoiding the pellet (which may be invisible). Rinse with 200 μl of 70% ethanol chilled to −20° C. without disturbing the pellet. Let the pellet air dry 30 minutes.

Add to the dried pellet:
7.2 μl of Water
1 μl of 10×Ligation Buffer
1 μl of 10 mM ATP
0.8 μl T4 DNA Ligase
Incubate 20 hours at 14° C.
10×Ligation Buffer
200 mM Tris-HCl pH 7.6
100 mM $MgCl_2$
50 mM dithiothreitol 3. Packaging and plating the ligated genomic DNA These steps are performed as outlined for cDNA in steps II-B10 and 11, above, except that *E. coli* strain c600 or LE392 is used in place of strain BB4.

B. Identification of a Homologous Gene from the Genomic Library

Follow the protocol outlined in step II-C, above, with the following exceptions:

1. About 1 million plaques containing genomic DNA should be plated onto 20 plates (50,000 plaques/15 cm plate).

2. If a cDNA from the chosen species homologous to the cyclophilin cDNA selected from those in FIG. 1 is isolated, it should be radiolabelled and hybridized to the genomic library. Otherwise the cDNA selected from FIG. 1 should be used.

3a. If a cDNA from the chosen species is used to probe the genomic library, hybridization should be performed at 65° C. After hybridization, the filters should be washed first for 1 hour in 2×SSC at 65° C. and then for 30 minutes in 0.2×SSC at 65° C. before they are used to expose X-ray film. More stringent hybridization and wash conditions are possible when using a cDNA probe from the same species as the genomic library.

3b. If a cDNA selected from FIG. 1 is used to probe the genomic library, hybridization should be performed at 45° C. After hybridization, the filters should be washed in the same manner that was used to obtain discrete bands on the Southern blot in step I.

This procedure allows identification of plaques containing the gene of interest, which plaques are used in the next step. Individual plaques should be isolated from a second round of screening as described in IIC2, above. Individual hybridizing plaques from the second round of screening will represent clones of cyclophilin genes from the selected species.

C. Cloning the Promoter Region from Identified Phage

1. DNA which will contain the desired gene should be isolated from one or two identified phage.

To a 5 ml culture tube add:
150 μl of a saturated overnight culture of *E. coli* strain C600
10 million pfu of eluted phage Incubate at 37° C. for 30 minutes with gentle shaking. Add 4 mls of L-broth and incubate cultures at 37° C. with shaking until the culture clears (about 5 hours). Then add 100 μl of chloroform to the tube and continue 37° C. incubation for 15 minutes. Allow chloroform to settle before proceeding.

Transfer lysate to a 12 ml polypropylene culture tube. Cfg at 5,000 rpm for 10 minutes in a Sorvall ss34 rotor or equivalent. Transfer lysate into a 5 ml thick-walled polycarbonate tube for the Beckman 50.3 Ti rotor or equivalent being careful to avoid carrying any chloroform along. Add 5 μl of DNase @ 1 mg/ml and 10 μl of RNase @ 2 mg/ml. Mix and incubate on ice overnight. Cfg at 40,000 rpm for 1 hour, 4° C. Remove supernatant and leave the tube exposed to air until completely dry (30 minutes). Resuspend the pellet in 0.41 ml of SM buffer. Transfer 0.4 ml to a microfuge tube and allow to warm to room temperature.

Add to the tube:
1.5 μl of diethylpyrocarbonate (DEPC)
10 μl of 10% SDS
90 μl of Tris/EDTA (combine 1 ml of 2M Tris, unadjusted for pH, with 0.8 ml of 0.25M EDTA pH8.0)

Mix and place closed tubes @ 70° C. for 10 minutes. Remove and allow tube to. cool to room temperature. Then add 50 μl of 5M potassium acetate and mix. Incubate on ice 30 minutes. Then cfg @ 15,000 rpm, 4° C. for 15 minutes. Carefully transfer supernatant to a clean tube. Repeat cfg and transfer. Then add 1 ml of 95% ethanol and mix. Cfg for 5 minutes, remove supernatant, and wash pellet with 80% ethanol. Allow pellet to air dry. Resuspend pellet in 200 μl of TE(pH8.0) plus 0.3M sodium acetate. Then add 400 μl of ethanol and mix. Cfg for 5 minutes, remove supernatant, and wash pellet with 80% ethanol. Allow pellet to air dry. Dissolve pellet in 38 μl of TE(pH8.0) and 2 μl of RNase @ 2 mg/ml. The tube should contain 4–8 μg of phage DNA.

2. Identification of a genomic restriction fragment likely to contain the gene promoter by southern hybridization Digest the isolated phage DNA with each of the following restriction enzymes: EcoRI, HindIII, BamHI, PstI, XbaI, and SalI. For each digestion use:
2 μl of isolated phage DNA
2 μl of 10×restriction buffer (as suggested by the manufacturer)
1 μl of concentrated restriction enzyme
15 μl of water Incubate digestions at 37° C. for 3 hours. Then electrophorese the digested DNA across an agarose gel, immobilize it onto nylon membrane, and hybridize with either (1) a labelled 0.3–0.5 kb DNA fragment encompassing the 5'-most end of the cDNA from the chosen species (stepIIE-3) or (2) a labelled 0.3–0.5 kb fragment encompassing the 5'-most end of the cyclophilin cDNA chosen from FIG. 1 that was used to isolate the genomic clone. Use the protocol detailed in I-B through I-D. Use the guidelines in B-3a or B-3b, above (whichever is applicable), for hybridization and washing conditions.

Using this procedure it should be possible to identify a restriction fragment between 5 and 10 kb in size which contains the desired coding sequence. A fragment this large will probably also contain the region adjacent to the 5' end of the coding sequence constituting the promoter of this gene.

3. Cloning the genomic fragment likely to contain the desired promoter into *E. coli.*

Repeat the restriction digest in step 2 which produced the restriction fragment between 5 and 10 kb in size which hybridized to the probe using 5 μl of phage DNA. Isolate this fragment from an agarose gel using DEAE cellulose as described in step IIIA-2, except that no phage DNA is added before ethanol precipitation. Resuspend the DNA in 20 μl of water.

Digest 1 μg of pUC119 DNA with the same restriction enzyme used to isolate the fragment above under the same conditions. Following digestion, add 1 unit of calf alkaline phosphatase (Boerhinger Mannheim) and incubate at 37° C. for 30 minutes. Then add sodium acetate to a final concentration of 0.3M and 2 volumes of ethanol. Chill on dry ice and cfg @ 15,000 rpm for 10 minutes in a microfuge to pellet the DNA. Remove the supernatant, wash the pellet with 80% ethanol and let air dry. Dissolve the DNA in 20 μl of water.

In a microfuge tube add:

1 μl of digested, phosphatased pUC119 DNA

5 μl of the purified restriction fragment

3 μl of 10×Ligation Buffer

3 μl of 10 mM ATP

2 μl of T4 DNA Ligase

16 μl of sterile water

Incubate overnight at 14° C. Transformation of *E. coli* can be accomplished by standard methods. Described below is a general method that is applicable.

Grow a culture of the desired *E. coli* strain to saturation in L-broth. Cfg culture at 10,000 g for 5 minutes to pellet cells. Remove supernatant and resuspend cells in ½ of original volume with cold 50 mM calcium chloride. Incubate on ice 30 minutes, then Cfg at 8000 g for 5 minutes. Remove supernatant, resuspend pellet in ¹⁄₁₀ of original volume with cold Calcium Chloride. Cells are now competent for transformation.

Into a sterile microfuge tube add 1 μl of plasmid DNA or ligated DNA and 200 μl of competent cells (see above). Incubate on ice for 30 minutes. Place in a 42° C. waterbath for 90 seconds, then back on ice for 1 minute. Add 1 ml of L-broth. Cfg for 15 seconds to pellet cells. Pour off supernatant, leaving about 100 μl. Resuspend pellet in remaining supernatant and plate onto L-agar+the appropriate antibiotic to select for cells containing the desired plasmid DNA. Incubate at 37° C. overnight. Colonies appearing on selection plate can be screened for the presence of the desired plasmid. Transform into *E. coli* strain JM101 and spread over a plate containing L-agar plus 200 μg/ml ampicillin, 0.004% X-gal. and 200 μM IPTG. Incubate the plate at 37° C. overnight. Non-blue colonies which appear on the plate should contain the gene fragment inserted into pUC119. Grow 2 ml cultures of 10 of these colonies and prepare miniprep plasmid DNA from them (step IIE-1). Identify and map a plasmid containing the gene insert by restriction digestion and subsequent electrophoresis. It may be possible to tentatively identify the specific region in the genomic fragment which contains the gene by comparing its restriction map with that of the cDNA.

4. Identifying the promoter-leader/coding sequence junction

Repeat steps 2 and 3 above, using the plasmid DNA from step 3 to identify and clone a smaller restriction fragment (2 kb or less) which hybridizes to the 5' end of the cDNA. Sequence this cloned DNA by the dideoxy method using a sequenase kit available from U.S. Biochem. Co. according to the manufacturer's instructions or by any other preferred method. Sequencing with the M13 −20 primer and the reverse primer (Stratagene) will provide sequence from both ends of the cloned DNA. Comparison of the sequence obtained with the chosen cyclophilin cDNA from FIG. 1 or the homologous cDNA (if available) should allow identification and orientation of the gene within the genomic fragment. This information is used to determine where the promoter-leader/coding sequence junction is in the genomic fragment. If this sequence is not included, continue sequencing with 20 nucleotide primers made identical to the end of the previous sequence until it is obtained. These primers can be ordered from Pharmacia LKB or any other preferred supplier.

The size of the region 5' to the coding sequence in the isolated genomic fragment(s) should be determined from the location of the leader/coding sequence junction. If this region is less than 2 kb, it will be necessary to isolate another genomic fragment containing a larger region upstream of the coding sequence. This is accomplished by repeating step C with another phage from step B until one containing this upstream region is identified.

5. Introducing a convenient restriction site at the promoter leader/coding sequence junction a. Mutagenesis primer—Using the junction sequence obtained in step 4, obtain a synthetic oligonucleotide that contains 20 nucleotides of homology spanning the leader/coding sequence junction with a restriction enzyme recognition sequence inserted into the leader immediately adjacent to the start of the coding sequence (Pharmacia LKB or any preferred supplier). Choose an enzyme recognition sequence that can be conveniently used to subclone a promoter-leader fragment at least 1 kb in size from the total genomic fragment, i.e. one that is not present in the promoter region.

b. Single stranded template preparation—Transform the pUC119 plasmid containing the gene insert from step 3 into a dut/ung *E. coli* strain such as *E. coli* strain CJ236 (Biorad, Richmond, Calif.) or the like. Use this to inoculate 2 ml of L-broth+200 μg/ml ampicillin. Incubate at 37° C., shaking until the culture is slightly turbid (about 50 Klett units). Then add helper phage M13K07(ca. 10 million pfu) or VCSM13 (Stratagene) and continue 37° C. incubation overnight.

Aliquot 1.5 ml of culture into a microfuge tube. Cfg for 15 seconds and transfer supernatant into a clean tube. Cfg for 5 minutes and transfer 1.2 ml of supernatant into clean tube. Add 180 μl of 2.5M NaCl, 20% polyethylene glycol, mix thoroughly. Incubate at room temp. for 15 minutes. Cfg for 5 minutes, discard supernatant completely. Resuspend pellet in 200 μl of TE buffer. Heat for 5 minutes @ 55° C., mix. Add 100 μl of phenol, mix. Heat for 5 minutes @ 55° C. Add 100 μl of chloroform, mix. Leave at room temperature for 5 minutes. Mix well, then cfg for 5 minutes. Transfer 160 μl of upper phase into a new tube. Add 20 μl of 3N sodium acetate (pH4.5) and 400 μl of cold ethanol into new tube. Chill on dry ice, then cfg for 5 minutes. Remove supernatant, add 200 μl of 80% ethanol, cfg 5 more minutes. Remove supernatant and let air dry. Resuspend pellet in 20 μl of TE, electrophorese 2 μl on agarose gel to quantitate (compare UV intensity with known amount of DNA).

c. Kinasing mutagenesis primer

To a microfuge tube add:

50 pmol of mutagenesis primer

1 μl of 10×ligation buffer 10 mM ATP

1 μl of Kinase (10 units)

Add water to 10 μl final volume. Incubate at 37° C. for 30 minutes, then at 70° C. for 5 minutes.

d. Annealing template to primer

To a microfuge tube add:

500 ng of template (b)

2 μl of kinased mutagenesis primer (c)

2 μl of 10×Hin buffer

Add water to 20 μl total volume. Place sample in a beaker of water @ 90° C., let cool to room temperature.

10×Hin buffer contains:
66 mM Tris, pH7.4
66 mM NaCl
66 mM magnesium dichloride
50 mM DTT
e. Fill-in reaction
To a microfuge tube add:
20 μl of NTP mix
20 μl of annealed template primer (d)
3 μl of T4 ligase (about 1000 units)
2 μl of DNA polymerase, klenow enzyme (about 10 units)
Incubate overnight at 15° C.
Add 2 μl more of T4 ligase, incubate 2 more hours at 15° C.

NTP mix:
6 μl of 10×Hin buffer
12 μl of 5 mM dATP
12 μl of 5 mM dCTP
12 μl of 5 mM dGTP
12 μl of 5 mM dTTP
6 μl of 10 mM ATP
f. Transformation
Use 20 μl of the fill-in reaction (e) to transform *E. coli* strain JM101. Cells are plated onto L-agar+200 μg/ml ampicillin. Some of the colonies which grow on this plate should contain the desired pUC119 gene plasmid from step C-3 with the mutagenesis primer (a) incorporated.
g. Screening for desired plasmid
Plasmid DNA is made from ampicillin resistant colonies (f) using the protocol in step IIE-1. This DNA is digested with the restriction enzyme which recognizes the sequence incorporated into the mutagenesis primer (a) and run on an agarose gel. In this way a plasmid which is cut at the promoter-leader/coding sequence junction with this enzyme can be identified. Sequence surrounding the mutagenesis site on the plasmid should then be verified.
6. Isolating the promoter region
Using the information obtained from mapping the promoter region, digest the plasmid DNA from step 5(g) above with restriction enzymes which will release a promoter fragment starting at the leader/coding sequence junction and extending at least 1 kb upstream. This fragment can be isolated from agarose gel using DEAE cellulose as described in step IIIA-2 except that no phage DNA is added before ethanol precipitation.

The isolated fragment can be utilized in a selected chimeric gene construction, cloned into any desired vector and transformed into plant cells to express a selected heterologous structural coding sequence in essentially all organs of the plant. A promoter region isolated from *B. napus* was operably linked to reporter genes and transformed into plant cells to test the activity of the promoter region (see example 2). Any promoter region isolated pursuant to this invention can be tested in a similar manner. Transformed plants containing a promoter region that directs high levels of transcription of a heterologous gene to which it is operably linked can be obtained by standard methods known to those skilled in the art.

Although some degree of variability in performance may be expected between cyclophilin promoters from different plant species, the exhibited activity of the *Brassica napus* cyclophilin promoter in other plants such as cotton, soybean and tomato, suggests the utility of a given cyclophilin promoter is not confined to a particular species. Preferably, the promoter from the species to which it will be introduced is used as the promoter of choice.

Illustrative monocots useful for transformation and transcription of vectors containing coding sequences under the control of the plant cyclophilin promoter include asparagus, rice, maize, barley, orchard grass, wheat and rye.

Illustrative dicots useful for transformation and transcription of vectors containing coding sequences under the control of the plant cyclophilin promoter include tomato, potato, tobacco, lettuce, sunflower, oilseed rape, flax, cotton, sugarbeet, celery, soybean, alfalfa, cucumber, carrot, cauliflower and other Brassica species.

Any recombinant vector capable of genomic integration or autonomous replication can be used with the cyclophilin promoters. Illustrative vectors include pMON200 and pMON505 (S. G. Rogers et al., *Methods Enzymol.*, 53:253 (1987)). Vectors in current use have convenient multilinker regions, which may be flanked by a promoter and a polyadenylate addition site for direct expression of inserted coding sequences (S. G. Rogers et al., *Methods Enzymol.*, 53:253 (1987)). Modern plant transformation vectors are capable of replication in *Escherichia coli* as well as Agrobacterium (H. Klee and S. G. Rogers, in Plant DNA Infection Agents, T. Hohn and J. Schell, Eds., Springer-Verlag, New York, 1985, pp. 179–203). The principal requirments are that the DNA be capable of entering a host cell and capable of integrating into a host genome or capable of undergoing replication in the host cell and should, in addition, have a genetic determinant through which it is possible to select those host cells which have received the DNA. Such laboratory methods as referenced in T. Maniatis et al. (1982) *Molecular Cloning, A Laboratory Manual* (Cold Spring Harbor Laboratories, Cold Spring Harbor, N.Y.), incorporated herein by reference, are well known for carrying out DNA preparation including synthesis, restriction site preparation ligation and transformation.

Chimeric genes suitable for expression in plant hosts include those responsible for herbicide tolerance, insect resistance and disease resistance. Specific examples of suitable heterologous genes include the genes for *Bacillus thuringiensis* (B.t.) toxin (D. A. Fischhoff et al., *Bio/Technology* 5:807 (1987); M. Vaeck et al., *Nature* 238:33 (1987); and D. M. Shah et al., *Science* 233:478 (1986)) and coat protein genes of plant viruses like tobacco mosaic virus (TMV), cucumber mosaic virus (CMV), alfalfa mosaic virus (ALMV), potato virus X (PVX) and potato virus Y (PVY) (C. S. Gasser and R. T. Fraley, *Science* 244:1293 (1989)).

All plants, both monocotyledons (monocots) and dicotyledons (dicots), are capable of transformation and subsequent transcription of chimeric genes, containing coding sequences under control of the plant cyclophilin promoter. A list of plant species for which the production of transgenic plants have been reported is found in C. S. Gasser and R. T. Fraley, *Science* 244:1293 (1989). Transformation has been demonstrated for plant species such as petunia, tomato, potato, tobacco, Arabidopsis, lettuce, sunflower, oilseed rape, flax, cotton, sugarbeet, celery, soybean, alfalfa, *medicago varia*, lotus, *vigna aconitifolia*, cucumber, carrot, cauliflower, horseradish, morning glory, poplar, walnut, apple, asparagus, rice, corn, orchard grass and rye.

Transformation and DNA delivery methods useful with vectors containing the plant cyclophilin promoters are not limited to any particular method. Illustrative methods include the use of virus, pollen, *Agrobacterium tumefaciens* and the free DNA delivery methods such as the use of protoplasts, lip osomes, microinjection, electroporation, and high-velocity microprojectile technology or "particle guns" (T. Klein et al., *Biotechnology* 6:559 (1988)). Plant transformation can be achieved in plant protoplasts through facilitation of DNA uptake by calcium phosphate precipitation, polyethylene glycol treatment, electroporation, or combinations of the treatments (I. Potrykus et al., *Mol. Gen. Genet.* 199:183 (1985); H. Lorz et al., ibid., p. 178; M. Fromm et al., *Nature* 319:791 (1986); H. Uchimiya et al., *Mol. Gen. Genet.* 204:204 (1986)). Transformed plant cells can be regenerated into differentiated plants using standard nutrient media supplemented with selected shoot-inducing or root-inducing hormones or by other methods known in the art (see for example S. G. Rogers et al. *Methods in Enzymology* 118:627 (1986)).

Although the invention has been described with respect to specific modifications, the details thereof are not to be construed as limitations, for it will be apparent that various equivalents, changes and modifications may be resorted to without departing from the spirit and scope thereof and it is understood that such equivalent embodiments are to be included therein.

EXAMPLES

Example 1

Isolation of Cyclophilin Promoter from Tomato

A. Isolation of a cDNA for Cyclophilin from a Tomato cDNA Library

A cDNA library is constructed from RNA isolated from a collection of the upper 0.5 cm of tomato plants (c.v. UC82B). The tissue of the upper 0.5 cm of the plant consists of young leaves, floral buds less than 3 mm in length, a section of young stem tissue, and the vegetative shoot apex and associated organ primordia. PolyA$^+$RNA is isolated from the total RNA by chromatography over oligo (dT) cellulose (Collaborative Research, Inc., Bedford, Mass.).

Approximately 1 μg of the PolyA$^+$RNA is used to synthesize double stranded cDNA using a cDNA synthesis kit (Amersham Inc., Arlington, Ill.). EcoRI sites in the cDNA are protected from digestion by treatment with EcoRI methylase (New England Biolabs, Beverly, Mass.). EcoRI linkers (New England Biolabs, Beverly, Mass.) are ligated onto the cDNA and the mixture digested with EcoRI. The cDNA is size fractionated and separated from unattached EcoRI linkers by electrophoresis on a 0.8% Sea Plaque (FMC Corp., Philadelphia, Pa.) agarose gel. The cDNA greater than 400 bp in length is extracted from the gel on NA45 diethylaminoethyl (DEAE) membrane (Schleicher and Schuell, Keene, N.H.). The cDNA is ligated into the cDNA cloning vector Lambda-ZAP (Stratagene, LaJolla, Calif.). The ligated material is packaged into phage particles using GigaPack Gold packaging extracts (Stratagene). Packaging of one-third of the material resulted in 3×10$^5$ plaque forming units (pfu).

15,000 plaques from this library are screened with $^{32}$P-labelled single stranded cDNA probes made from PolyA$^+$ RNA isolated from young tomato flower buds (less than 4 mm in length) and made from RNA isolated from tomato seedlings. Plaques giving strong signals with both these probes would derive from highly expressed mRNAs in those tissues. The filters are eluted and probed with total tomato genomic DNA that has been labelled with $^{32}$P by the random oligonucleotide priming method (Feinberg and Vogelstein, *Anal. Biochem.* 132:6 (1983)). Plaques hybridizing strongly with this probe represent those RNAs from genes which are present in multiple copies in the genome. Those showing no signal derive from genes present in only one to five copies in the tomato genome. By using this method, 45 plaques were identified as putative candidates for clones deriving from highly expressed, low copy number genes. After secondary screening and plasmid rescue from Lambda-ZAP (which results in clones in the plasmid pBSSK-(Stratagene)), 21 of the cDNAs are shown to express at relatively low levels, or to come from multi-copy genes and are eliminated from further testing. DNA is isolated from the remaining 24 clones and digested with EcoRI to release the inserts which range in size from 250 bp to over 2.0 kb. Agarose gels of the DNA are blotted and hybridized with the same two probes used in the screening to verify their expression pattern in a more sensitive assay. Four of the clones show strong signals with the young flower bud probe. Cross-hybridization experiments are performed using a probe made from a tomato ribulose bisphosphate carboxylase small subunit clone and with each of the four clones to ensure that none of the new clones are homologous to the previously isolated gene or to each other. No hybridization is observed with these probes.

The four initial clones are further characterized by labelling with the random primer method and probing Southern blots containing digested tomato genomic DNA and controls for gene copy number. All four clones are found to derive from genes with low copy number in the tomato genome. The level of expression of these cDNAs in the tomato tissues is examined by Northern blot analysis. RNA is isolated from the following organs; young flower buds (0–4 mm), young leaves (2 cm), apices (2 mm), and mature anthers. 20 μg of total RNA from each tissue is run on a formaldehyde/agarose gel and blotted to Genescreen (DuPont, Boston, Mass.) membrane. The four cDNA clones are labeled by the random primer method and used to probe the Northern blots of RNA from various tomato tissues. Signals are detected in some tissues with all the clones after a 4 hour exposure, indicating high levels of expression. One of the clones, designated pMON9976, shows very strong expression in all tissues tested, as determined by observing the high intensity of the bands in all lanes. A partial nucleotide sequence. of this clone was determined (FIG. 1). A homology search of the GeneBank database of nucleotide sequences shows that the insert of pMON9976 encodes a protein that shows a high degree of identity to mammalian cyclophilin.

B. Isolation of a Tomato Genomic Clone for Cyclophilin and Identification of the Promoter Region Tomato genomic DNA is purified in substantial accordance with the method of N. Kislev and I. Rubenstein, *Plant Physiol.* 66:1140 (1980). The DNA is partially digested with restriction endonuclease MBoI (New England Biolabs, Beverly, Mass.). That portion of the restriction fragments that are between 12 kb and 24 kb in length are isolated by sucrose gradient centrifugation (T. Maniatis et al., *Molecular Cloning, A Laboratory Manual* (Cold Spring Harbor Laboratory, 1982)). These fragments are ligated into the bacteriophage lambda cloning vector EMBL3 (Stratagene) which has been digested with BamHI and EcoRI. The ligation mixture is packaged into phage particles as described herein. 1.6×10$^6$ pfu were plated on *E. coli* BNN 102 (Young and Davis, *Proc. Natl. Acad. Sci.USA* 80:1194 (1983)) for amplification.

For isolation of a genomic clone for the tomato cyclophilin gene the amplified library is screened with a $^{32}$P-labelled pMON9976 (See Section A of Example 1). DNA isolated from hybridizing plaques is mapped by restriction digestion and Southern blotting analysis. The promoter region is identified as that set of sequences just upstream of the cyclophilin coding sequence. A 1 kb to 4 kb fragment from this region is then subcloned and engineered to allow attachment to other coding sequences, and an appropriate 3'-sequence. Introduction of the resulting plasmid into plants leads to production of the protein encoded by the sequence in the transgenic plants.

Example 2

Isolation of the Cyclophilin Promoter Region from Oilseed Rape (*Brassica napus*)

A. Isolation of a cDNA for *B. napus* Cyclophilin

RNA is isolated from *B. napus* flower buds less than 4 mm in length. PolyA+RNA is purified from total RNA by chromatography over oligo-dT cellulose. A cDNA library is constructed in the plasmid vector pTZ18R-B using materials available from Invitrogen (San Diego, Calif.). 4,500 bacteria, harboring recombinant plasmids, are plated and nitrocellulose replicas of the plates screened with $^{32}P$ labelled inserts from pMON9976. Hybridizing colonies are isolated and replated. A second round of screening is performed with the pMON9976 probe and hybridizing plaques are again isolated. The sequence of several of the clones is determined and found to encode cyclophilin-homologous proteins (FIG. 2). The sequences of all clones examined are identical. One of the clones, designated pMON8612, is chosen for further characterization.

B. Comparison of *B. Napus* Cyclophilin Expression and Expression from the 35S Promoter as Indicated by Message Levels in Various Plant Organs In one experiment the levels of *B. napus* cyclophilin message in various organs is compared to the levels produced by an introduced (J. Fry et al., *Plant Cell Rep.* 6:321 (1987)) chimeric gene driven by the 35S promoter in a *Brassica napus* plant. In this case the coding region of the chimeric gene is from Arabidopsis 5-enolphyruvyl-3-phosphoshikimate (EPSP) synthase (H. Klee et al., *Mol. Gen. Genet.* 210:282 (1987)). The level of expression from the 35S promoter will vary between individual independent transgenic plants (P. Sanders, et al., *Nucleic Acids Res.* 15:1543 (1987)). The plant used in this experiment is the highest expressor of a set of more than 110 independent transformants. The level of the 35S driven transcript is higher in leaves than the level of the cyclophilin transcript, however, the cyclophilin transcript is present at higher levels in young buds and immature anthers. The level of cyclophilin expression is also high in roots.

C. Isolation of Genomic Clones for *B. napus* Cyclophilin

DNA is isolated from *B. napus* c.v. westar leaves in substantial accordance with the method of N. Kislev and I. Rubenstein, *Plant Physiol.* 66:1140 (1980). The DNA is partially digested with restriction endonuclease MBoI. The DNA is electrophoreesed on an agarose gel and fragments of 12 kb to 24 kb are isolated on NA45 DEAE membrane and a library is constructed in substantial accordance with the teaching of Example 1A. The library is screened with a 600 bp BglII/HindIII fragment of pMON8612 and four hybridizing clones isolated.

D. Construction of Plant Transformation Vectors with the *B. napus* Cyclophilin Promoter A 3.6 kb BglII fragment from one of the *B. napus* genomic clones that hybridized to labeled cyclophilin cDNA is subcloned into pBSKS+ (Stratagene), resulting in pMON8635, the plasmid is mapped and partially sequenced. The sequence showed that this DNA fragment contained the 5' end of the cyclophilin coding sequence and 3.1 kb of the 5' flanking DNA. A ClaI site is engineered one base pair upstream of the ATG start codon of the cyclophilin coding sequence by oligonucleotide mediated mutagenesis in substantial accordance with the method of Kunkel, *Proc. Natl. Acad. Sci. USA*. 82:488 (1985). The 5' flanking DNA of the cyclophilin gene (2.9 kb) can be isolated as a ClaI to XhoI DNA fragment. A chimeric gene is constructed by fusing the ClaI to XhoI fragment to the *E. coli* β-glucuronidase (GUS) (R. Jefferson et al.,*EMBO J.* 6:3901 (1987)) reporter coding sequence and the polyadenylation region 3'-end of the 7 S seed storage protein gene of soybean (M. Schuler et al., *Nucleic Acids Research* 10:225 (1982)), resulting in pMON8658.

A particle gun transformation system (T. Klein et al., *Biotechnology* 6:559 (1988) is used to perform transient assays with the cyclophilin/GUS gene to evaluate the function of the promoter. Plasmid pMON8658 DNA is precipitated onto tungsten particles and blasted into young *B. napus* leaves, cotton cotyledons, and soybean cotyledons as described by T. Klein et al., *Bio/Technology* 6:559 (1988). The leaves are incubated overnight and then stained with a histochemical substrate, 5-bromo-4-chloro-3-indoyl-β-D-glucuronide (Sigma, St. Louis, Mo.). Cells containing active GUS enzyme will stain blue with this compound (R. Jefferson, et al., *EMBO J.* 6:3901 (1987)). Numerous blue spots are visible on all tissues that have been blasted with the pMON8658 coated particles, demonstrating that the *B. napus* cyclophilin promoter is active in *B. napus*, cotton, and soybean.

The cyclophilin/GUS fusion gene is excised from pMON8658 on a NotI restriction endonuclease fragment and subcloned into pMON987, a vector for Agrobacterium mediated plant transformation, resulting in pMON8667. The pMON987 construct is made up of the following segments of DNA. The first is the 3.1 kb SalI to PvuI segment of pBR322 (ori-322) which provides the origin of replication for maintenance in *E. coli* and the bom site for conjugal transfer into *A. tumefaciens* cells. The next segment is the 0.36 kb PvuI to BclI fragment from pTiT37 that carries the nopaline-type T-DNA right border (R. T. Fraley et al., *Bio/Technology* 3:629 (1985). It is joined to a 4.7 kb chimeric gene consisting of the enhanced CaMV 35S promoter (R. Kay et al., *Science* 236:1299, (1987)), a variant *A. thaliana* EPSP synthase coding region (described below), and the NOS 3' polyadenylation signal. The next segment is a 0.93 kb fragment (AvaI to an engineered EcoRV site) isolated from transposon Tn7 that encodes bacterial spectinomycin/streptomycin resistance (Spc/Str), and is a determinant for selection in *E. Coli* and *Agrobacterium tumefaciens*. This is joined to the 1.5 kb segment of DNA encoding a chimeric gentamicin resistance gene which permits selection of transformed plant cells. The chimeric gene (P-35S/AAC(3)-III/NOS 3') consists of the CaMV 35S promoter, the gentamicin-3-N-acetyltransferase type III gene (AAC(3)-III) (M. Hayford et al. *Plant Physiol.*, 86:1216 (1988)) and the NOS 3' polyadenylation signal. The last segment is the 0.75 kb ori-V containing the origin of replication from the RK2 plasmid (Schmidhauser and Helinski *J. Bacteriol.* 164:446 (1985)). pMON8667 is introduced into tobacco and *B. napus* plants as described by R. Horsch et al., *Proc. Natl. Acad. Sci. USA* 83:4428 (1986) and by J. Fry et al., *Plant Cell Rep.* 6:321 (1987)). Histochemical staining of tissue from these transgenic plants for GUS activity shows that the gene is active in leaves, stems, the shoot apex, and all organs of immature and mature flowers.

A vector for expression of a chimeric gene construct was made by ligating the promoter fragment of *B. napus* cyclophilin to the structural coding sequence for a glyphosate tolerant form of Arabidopsis EPSPS, resulting in pMON8654. The structual coding sequence for a glyphosate tolerant form of Arabidopsis EPSPS is obtained in the following manner. An *Arabidopsis thaliana* genomic library was prepared by cloning size fractionated (15–20 kb) MboI partially digested DNA into BamHI and EcoRI digested lambda EMBL3 (Stratagene Cloning Systems, San Diego, Calif.). Approximately 10,000 plaques of phage from this library were screened with $^{32}$P labeled petunia EPSP synthase probe (C. Gasser et al. *J. Biol. Chem.* 263:4280 (1988)). A strongly hybridizing plaque, designated E1, was purified. Southern blots of the phage DNA with the EPSP synthase probe identified two fragments which hybridized very strongly. The first fragment was a 1.0 kb HindIII fragment and the other was a 700 bp BamHI fragment. These fragments were subcloned into plasmid pUC119 (pUC119 is constructed by isolating the 476 bp Hgi AI/Dra I fragment of bacteriophage M13 and making the ends of the fragment blunt with T4 DNA polymerase (New England Biolabs). This fragment is then inserted into pUC19 (C. Yanisch-Perron et al., *Gene* 33:103 (1985)) that has been digested with Nde I and filled in with Klenow DNA polymerase (New England Biolabs)) and designated pMON574 and pMON578.

The DNA sequences for the two inserts were then determined by the method of Sanger et al., *Proc. Natl. Acad. Sci. USA*, 74:5463 (1977). The sequence data indicated that the phage did contain the EPSP synthase gene of Arabidopsis by its strong homology to the petunia EPSP synthase sequence. The 700 bp BamHI fragment was used as a hybridization probe against the phage and Arabidopsis genomic DNA to identify restriction fragments suitable for the cloning of the entire EPSP synthase gene. Two hybridizing BglII fragments of 6.0 kb and 3.2 kb were identified in the E1 phage clone. These fragments were separately subcloned into pMON550 (C. S. Gasser et al., *J. Biol. Chem.* 263:4280 (1988)) to provide DNA for further experiments and designated pMON582 and pMON583, respectively. Two additional subclones were made from clones pMON582 and pMON583. Plasmid pMON584 is the 1.8 kb EcoRI to BamHI fragment containing the 5'-end of the Arabidopsis EPSP synthase gene in pUC118 which is prepared from pUC18 in a manner analogous to the preparation of pUC119 from pUC19 described hereinbefore. Plasmid pMON589 is the 2.8 kb BamHI to a BglII fragment containing the 3'-end of the Arabidopsis EPSP synthase gene in pUC119. Sequence determination from the BamHI site of pMON584, and from the BamHI site of pMON589 completed the sequence of the coding regions of the gene.

The coding sequence was altered so that the expressed Arabidopsis EPSP synthase would include an alanine for glycine substitution at position 101 of the mature enzyme. Plasmid pMON578 was mutagenized with the oligonucleotide:

5'-CTTTACCTCGGTAATGCAGCTACAGCAATGCG-3' by the method of Kunkel, *Proc. Natl. Acad. Sci. USA*, 82:488 (1985). A portion of the resulting plasmid, pMON594, was sequenced to verify the mutation. pMON594 was then mutagenized with the oligonucleotide:

5'-TTGGTCTTAAGCAGCTTGACGCTGATGTTG-3' by the method of Kunkel (1985) to introduce an aspartate for glycine mutation at position 144 of the mature enzyme. The resulting plasmid was partially sequenced to verify the success of the mutagenesis. This construct containing the internal 730 bp BamHI fragment of the Arabidopsis EPSP synthase gene with the glycine (101) to alanine and glycine (144) to aspartic acid mutations was designated pMON9930.

A ClaI site is required just upstream of the translational initiation site for insertion of the Arabidopsis EPSP synthase gene into plant transformation/expression vectors. A 370 bp SnaBI/BamHI fragment of pMON584 including the translational initiation site and 65 bp of 5'-untranslated region was cloned into EcoRV/BamHI digested Bluescript KS$^+$ (Stratagene Cloning Systems, San Diego, Calif.) forming pMON9734.

The entire Arabidopsis gene was reconstructed for plant transformation experiments as follows: the 3.0 kb BamHI to BglII fragment containing the 3' half of the gene was excised from pMON583 and inserted into the unique BamHI site of pMON9734. This plasmid, pMON588, has a unique BamHI site in the middle of the gene. The 800 bp BamHI fragment from pMON9930 was then inserted into the unique BamHI site of pMON588. The resulting plasmid, pMON982, contains the entire EPSP synthase gene with the alanine for glycine substitution at position 101 and the aspartic acid for glycine substitution at position 144 of the mature protein. pMON982 was digested with ClaI and treated with Klenow polymerase in the presence of dATP, dCTP, TTP, and dGTP to produce a blunt end. The plasmid was then digested with Eco RI and the 3.5 kb fragment containing the entire variant Arabidopsis EPSP synthase coding region with the alanine for glycine substitution at position 101 and the aspartate for glycine substitution at position 144 of the mature protein is inserted into pMON979 under the control of the duplicated 35S promoter of CaMV (R. Kay et al., *Science* 236:1299 (1987)), resulting in pMON987 described hereinbefore.

The chimeric cyclophilin/Arabidopsis EPSP synthase gene is excised from pMON8654 on a NotI fragment and inserted into pMON987, which already includes a chimeric gene consisting of the E35S promoter of cauliflower mosaic virus (R. Kay et al., *Science* 236:1299 (1987)) fused to the coding sequence for the glyphosate tolerant form of Arabidopsis EPSPS as described above. The resulting plasmid is designated pMON8656. Plasmid pMON8656 contains two chimeric EPSPS genes driven by the cyclophilin and cauliflower mosaic virus (CaMV) E35S promoters. This construct is introduced into canola plants by the method of J. Fry et al., *Plant Cell Rep.* 6:321 (1987). These plants show tolerance to Roundup® herbicide (a herbicide made by Monsanto which contains glyphosate as the active ingredient, formulated as its isopropylamine salt).

Example 3

Isolation of the Cyclophilin Promoter Region from *Zea mays* (Maize)

A. Isolation of a cDNA for Maize Cyclophilin

A cDNA library is constructed from maize mature embryo RNA in the phage cloning vector Lambda-gt10 (Stratagene) by the method of C. Gasser et al., *Plant Cell* 1:15 (1989). Seven cyclophilin cDNA clones are isolated by screening this library with a 600 bp BglII/HindIII fragment of pMON8612 containing the coding region of the *B. napus* cyclophilin gene (See Example 2B). Several of these cDNAs are found to contain the complete coding sequence for maize cyclophilin (FIG. 1 and FIG. 2). The full-length cDNAs are subcloned from the phage into plasmid vectors. Sequencing confirms them to be authentic maize cyclophilin clones. Based on the frequency of cyclophilin cDNA clones present in the library the level of expression of cyclophilin in maize is also relatively high. The 800 bp EcoRI cDNA insert of one of these clones is inserted into pBSKS+ (Stratagene) to form pMON8712.

B. Isolation of Genomic Clones for Maize Cyclophilin and Isolation and Testing of the Promoter Region Genomic Southern analysis using pMON8712 as a probe indicates that there are 4–8 copies of genes with homology to cyclophilin in the maize genome. Plasmid pMON8712 is used to screen a maize genomic library purchased from Clontech Inc., Palo Alto, Calif. The isolated clones fall into five classes based on preliminary restriction analyses. A 5 kb fragment of one genomic clone (Lambda-Zmcyc15) containing the cyclophilin coding region and over 4 kb of 5'-flanking sequence is subcloned into PBSKS+ (Stratagene) for restriction mapping and sequence analysis. Approximately 250 bp of the genomic fragment showed 100% sequence identity with all of the cDNA clones isolated from a maize scutellum library that were sequenced. To facilitate constructions with the putative promoter region, a HindIII site is inserted approximately 1.7 kb from the cyclophilin start site and a BglIII site is engineered just upstream of the translation start site by the method of T. Kunkel, *Proc. Natl. Acad. Sci. USA* 82:488 (1985)). To construct a cassette vector for maize transformation the 1.7 kb HindIII-BglII fragment is used to construct a plasmid in which the promoter fragment is followed by a polylinker for inserting desired coding regions, followed by the polyadenylation region of the nopaline synthase 3'-end (A. Depicker et al., *J. of Mol. and App. Genetics* 1:561 (1982)). The coding sequences for GUS and a glyphosate tolerant form of maize EPSPS are inserted into the cassette vector producing pMON8779 and pMON8780 respectively. The coding sequence for a glyphosate tolerant form of maize EPSPS is obtained in the following manner. Maize seeds were imbibed for 12 hr in water, the embryos, including the scutella, were dissected from the seeds and RNA was purified from this material by the method of D. Rochester et al. *EMBO J.* 5:452 (1986). PolyA-mRNA was isolated from the RNA by chromatography on oligo dT cellulose, and was used to construct a cDNA library as described by C. S. Gasser et al. *Plant Cell*,1:15 (1989). The library was screened with a $^{32}$-P labelled RNA probe synthesized in vitro from a tomato EPSP synthase cDNA clone (C. Gasser et al. *J. Biol. Chem.* 263:4280 (1988)) which had been linearized with HindIII. The probe was synthesized with T7 RNA polymerase (Promega, Madison, Wis.). Hybridizing plaques were isolated, replated and nitrocellulose lifts from the plates were screened with the same probe. Plaques representing single clones which hybridized strongly to the tomato probe were isolated, propagated and used to prepare DNA. A clone designated lambda-z1d was found to contain a 1.8 kb EcoRI insert. The insert of this phage was subcloned into the EcoRI site of Bluescript KS+ (Stratagene, San Diego, Calif.) to form pMON9935. To facilitate future constructions an XbaI site was engineered immediately upstream of the first ATG initiation codon of this clone by oligonucleotide mediated mutagenesis by the method of Kunkel using the oligonucleotide:

5'-TACCAACCATCGGCGTCTAGAGGCAATGGCGGC-3' producing plasmid pMON9950. pMON9950 was digested with XbaI and religated to eliminate the 126 bp XbaI fragment at the 5' end of the cDNA forming pMON9951. To produce a coding sequence which encodes for a glyphosate tolerant form of maize EPSP synthase, pMON9951 was mutated by the method of Kunkel using the oligonucleotide:

5'-CTTCTTGGGGAATGCTGCTACTGCAATGCGGC-3' resulting in pMON9960. This mutagenesis will change a GGA codon to a GCT codon, changing the second glycine residue in the conserved sequence -L-G-N-A-G-T-A- to an alanine in the resulting protein. This coding sequence encodes a glyphosate tolerant form of maize EPSP synthase.

The GUS vector (pMON8779 described hereinbefore) is analyzed in particle gun assays in substantial accordance with the teaching of Example 2C. The results indicate that the 1.7 kb cyclophilin HindIII/BglII fragment drives GUS expression in maize leaves, but appears to be extremely weak when compared with the number and size of the blue spots obtained with the control E35S promoter. Since there are approximately five genes per haploid genome, as estimated by genomic Southern analysis, it is possible that one of the other genes is more highly expressed. Representatives of the other four classes of genomic clones are cloned and modified, as described above, to engineer vectors for expression of attached coding sequences. Vectors constructed in this manner allow for general expression of coding sequences in transgenic maize, and will be useful in engineering glyphosate tolerance in this or other grass species. For optimal expression in maize or other monocot species it may be desirable to add an intervening sequence that is efficiently spliced in monocots to the 5'-untranslated region or the coding sequence of the expression cassette as described by Callis et al., *Genes and Development*, 1:1183–1200 (1987)).

The above examples illustrate specific embodiments of the invention described herein. As would be apparent to skilled artisans, various changes and modifications are possible and are contemplated within the scope of the invention described.

What is claimed is:

1. A DNA molecule comprising an isolated plant cyclophilin promoter comprising at least 500 base pairs of a DNA sequence flanking 5' of a DNA sequence having more than 70% sequence homology with the plant sequences of FIG. 1, operatively linked to a structural coding sequence; wherein the plant cyclophilin promoter and the structural coding sequence are not naturally operatively linked.

2. A DNA molecule of claim 1 in which the plant cyclophilin promoter is from a dicotyledonous plant.

3. A DNA molecule of claim 1 in which the plant cyclophilin promoter is from a monocotyledonous plant.

4. A DNA molecule of claim 1 in which the plant cyclophilin promoter is selected from the group consisting of *Brassica napus*, maize and tomato.

5. The plant cyclophilin promoter of claim 4 which is a *Brassica napus* cyclophilin promoter.

6. The plant cyclophilin promoter of claim 4 which is a maize cyclophilin promoter.

7. The plant cyclophilin promoter of claim 4 which is a tomato cyclophilin promoter.

8. A plant transformation vector containing the plant promoter of claim 1.

9. A chimeric plant gene which comprises, operatively linked in sequence, a plant cyclophilin promoter of claim 1, a heterologous structural coding sequence, and a 3' non-translated sequence.

10. The chimeric plant gene of claim 9 in which the plant cyclophilin promoter is from a dicotyledonous plant.

11. The chimeric plant gene of claim 9 in which the plant cyclophilin promoter is from a monocotyledonous plant.

12. The chimeric plant gene of claim 10 in which the dicotyledonous plant is tomato.

13. The chimeric plant gene of claim 10 in which the dicotyledonous plant is *Brassica napus*.

14. The chimeric plant gene of claim 11 in which the monocotyledonous plant is maize.

15. A chimeric plant gene of claim 9 in which the structural coding sequence encodes a protein selected from the group consisting of *Bacillus thuringiensis* toxin protein, tobacco mosaic virus coat protein, cucumber mosaic virus coat protein, alfalfa mosaic virus coat protein, potato virus X coat protein, potato virus Y coat protein and a glyphosate tolerant 5-enolpyruvylshikimate-3-phosphate synthase (EPSPS).

16. The chimeric plant gene of claim 15 in which the structural coding sequence encodes *Bacillus thuringiensis* toxin protein.

17. The chimeric plant gene of claim 15 in which the structural coding sequence encodes cucumber mosaic virus coat protein.

18. The chimeric plant gene of claim 15 in which the structural coding sequence encodes alfalfa mosaic virus coat protein.

19. The chimeric plant gene of claim 15 in which the structural coding sequence encodes potato virus X coat protein.

20. The chimeric plant gene of claim 15 in which the structural coding sequence encodes potato virus Y coat protein.

21. The chimeric plant gene of claim 15 in which the structural coding sequence encodes a glyphosate tolerant 5-enolpyruvylshikimate-3-phosphate synthase (EPSPS).

22. The chimeric plant gene of claim 15 in which the structural coding sequence encodes tobacco mosaic virus coat protein.

* * * * *